(12) United States Patent
Roden et al.

(10) Patent No.: US 8,865,650 B2
(45) Date of Patent: Oct. 21, 2014

(54) THERAPY FOR COMPLICATIONS OF DIABETES

(71) Applicant: AbbVie Deutschland GmbH & Co. KG, Wiesbaden (DE)

(72) Inventors: Robert L. Roden, Foster City, CA (US); Richard J. Gorczynski, Westminster, CO (US); Michael J. Gerber, Denver, CO (US)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 14/079,464

(22) Filed: Nov. 13, 2013

(65) Prior Publication Data

US 2014/0073574 A1    Mar. 13, 2014

Related U.S. Application Data

(63) Continuation of application No. 13/766,266, filed on Feb. 13, 2013, now Pat. No. 8,623,819, which is a continuation of application No. 12/196,635, filed on Aug. 22, 2008.

(60) Provisional application No. 60/957,300, filed on Aug. 22, 2007.

(51) Int. Cl.
| | |
|---|---|
| *A61K 45/06* | (2006.01) |
| *A61K 31/549* | (2006.01) |
| *A61K 31/505* | (2006.01) |
| *A61K 31/4025* | (2006.01) |

(52) U.S. Cl.
CPC ............. *A61K 31/4025* (2013.01); *A61K 45/06* (2013.01); *A61K 31/549* (2013.01); *A61K 31/505* (2013.01)
USPC ........................... 514/15.4; 514/6.8; 514/16.2

(58) Field of Classification Search
CPC .. A61K 45/06; A61K 31/549; A61K 31/4025
USPC ......................................... 514/15.4, 16.2, 6.8
See application file for complete search history.

(56) References Cited

U.S. PATENT DOCUMENTS

| | | | |
|---|---|---|---|
| 5,567,713 A | 10/1996 | Cullinan et al. | |
| 5,622,971 A | 4/1997 | Winn et al. | |
| 5,731,434 A | 3/1998 | Winn et al. | |
| 5,767,144 A | 6/1998 | Winn et al. | |
| 6,121,416 A | 9/2000 | Clark et al. | |
| 6,162,927 A | 12/2000 | Winn et al. | |
| 6,197,780 B1 | 3/2001 | Münter et al. | |
| 6,238,708 B1 | 5/2001 | Hayek et al. | |
| 6,329,384 B1 | 12/2001 | Münter et al. | |
| 6,352,992 B1 | 3/2002 | Kirchengast et al. | |
| 6,380,241 B1 | 4/2002 | Winn et al. | |
| 6,420,412 B2 * | 7/2002 | Palepu et al. | ........... 514/397 |
| 6,462,194 B1 | 10/2002 | Winn et al. | |
| 6,559,188 B1 | 5/2003 | Gatlin et al. | |
| 6,946,481 B1 | 9/2005 | Winn et al. | |
| 7,208,517 B1 | 4/2007 | Winn et al. | |
| 7,365,093 B2 | 4/2008 | Winn et al. | |
| 7,445,792 B2 | 11/2008 | Toner et al. | |
| 8,057,813 B2 | 11/2011 | Toner et al. | |
| 8,257,724 B2 | 9/2012 | Cromack et al. | |
| 8,257,725 B2 | 9/2012 | Cromack et al. | |
| 2002/0055457 A1 | 5/2002 | Janus et al. | |
| 2003/0022811 A1 | 1/2003 | Singh et al. | |
| 2003/0092757 A1 | 5/2003 | Singh et al. | |
| 2004/0186083 A1 | 9/2004 | McMahon et al. | |
| 2005/0107354 A1 | 5/2005 | Koizumi et al. | |
| 2005/0113306 A1 | 5/2005 | Janus et al. | |
| 2005/0113307 A1 | 5/2005 | Janus et al. | |
| 2005/0214294 A1 | 9/2005 | Flyvbjerg et al. | |
| 2006/0035867 A1 | 2/2006 | Janus et al. | |
| 2006/0063825 A1 | 3/2006 | Dziki et al. | |

(Continued)

FOREIGN PATENT DOCUMENTS

| | | |
|---|---|---|
| DE | 19743140 A1 | 4/1999 |
| DE | 19743142 A1 | 4/1999 |

(Continued)

OTHER PUBLICATIONS

Torre-Amione G., et al., "Hemodynamic and Clinical Effects of Tezosentan, an Intravenous Dual Endothelin Receptor Antagonist, in Patients Hospitalized for Acute Decompensated Heart Failure," Journal of the American College of Cardiology, 2003, vol. 42 (1), pp. 140-147.

Torre-Amione G., et al., "Hemodynamic Effects of Tezosentan, an Intravenous Dual Endothelin Receptor Antagonist, in Patients with Class III to IV Congestive Heart Failure," Circulation, 2001, vol. 103 (7), pp. 973-980.

Valeant Pharmaceuticals North America LLC, Label for Enalapril, Jan. 30, 2012, pp. 1-20.

Watson A.M., et al., "The Endothelin Receptor Antagonist Avosentan Ameliorates Mephropathy and Atherosclerosis in Diabetic Apolipoprotein E Knockout Mice," Diabetologia, 2010, vol. 53 (1), pp. 192-203.

(Continued)

*Primary Examiner* — Julie Ha

(74) *Attorney, Agent, or Firm* — Neal, Gerber & Eisenberg LLP

(57) ABSTRACT

A method for enhancing glycemic control and/or insulin sensitivity in a human subject having diabetic nephropathy and/or metabolic syndrome comprises administering to the subject a selective endothelin A ($ET_A$) receptor antagonist in a glycemic control and/or insulin sensitivity enhancing effective amount. A method for treating a complex of comorbidities in an elderly diabetic human subject comprises administering to the subject a selective $ET_A$ receptor antagonist in combination or as adjunctive therapy with at least one additional agent that is (i) other than a selective $ET_A$ receptor antagonist and (ii) effective in treatment of diabetes and/or at least one of said comorbidities other than hypertension. A therapeutic combination useful in such a method comprises a selective $ET_A$ receptor antagonist and at least one antidiabetic, anti-obesity or antidyslipidemic agent other than a selective $ET_A$ receptor antagonist.

32 Claims, 1 Drawing Sheet

(56) References Cited

U.S. PATENT DOCUMENTS

| | | | |
|---|---|---|---|
| 2006/0074058 | A1 | 4/2006 | Holmes et al. |
| 2006/0135596 | A1 | 6/2006 | Zhang |
| 2006/0189675 | A1 | 8/2006 | King |
| 2007/0123582 | A1 | 5/2007 | Zhang |
| 2008/0132710 | A1 | 6/2008 | Henry et al. |
| 2008/0161321 | A1 | 7/2008 | Feldman et al. |
| 2010/0184026 | A1 | 7/2010 | Lesniewski et al. |

FOREIGN PATENT DOCUMENTS

| | | | |
|---|---|---|---|
| DE | 19744799 A1 | 4/1999 | |
| EP | 0647449 A1 | 4/1995 | |
| EP | 885215 B1 | 4/2006 | |
| WO | 9606095 A1 | 2/1996 | |
| WO | 9730045 A1 | 8/1997 | |
| WO | 9906397 A2 | 2/1999 | |
| WO | 0015599 A1 | 3/2000 | |
| WO | 0211713 A2 | 2/2002 | |
| WO | 0217912 A1 | 3/2002 | |
| WO | 02085351 A1 | 10/2002 | |
| WO | 2004082637 A2 | 9/2004 | |
| WO | 2006034084 A1 | 3/2006 | |
| WO | 2006034085 A1 | 3/2006 | |
| WO | 2006034094 A1 | 3/2006 | |
| WO | 2006034234 A1 | 3/2006 | |

OTHER PUBLICATIONS

Webb M.L., et al., "Endothelin Receptors as a Potential Therapeutic Target in the Treatment of Cardiovascular Disease: Rationale for Selective Antagonism of the ETa Subtype," DN&P, 1996, vol. 9 (6), pp. 348-350.

Weber, et al., [online], 2006 [retrieved on May 16, 2006]. Retrieved from the Internet< URL: http://www.seeinfo.com/dvidn.vbz.d.hrm>.

Weber M.A., et al., "A Selective Endothelin-Receptor Antagonist to Reduce Blood Pressure in Patients with Treatment-Resistant Hypertension: a Randomised, Double-Blind, Placebo-Controlled Trial," Lancet, 2009, vol. 374 (9699), pp. 1423-1431.

Weber M.A., et al., Darusentan Reduces 24-Hour Ambulatory Blood Pressure in Patients with Resistant Hypertension [online], May 2006 [retrieved on Aug. 20, 2007]. Retrieved from the Internet< URL: http://www.secinfo.com/dvjdn.vbz.d.htm>.

Wenzel, et al., [online], 2002. Retrieved from the Internet< URL: http://www.redorbitcomlnews/health/303255/spp301_phase_lib_results_in_diabetic_nephropathy_presented_at_asn/index.html?source=r_health>.

Wenzel R.R., et al., "Avosentan Reduces Albumin Excretion in Diabetics with Macroalbuminuria," Journal of the American Society of Nephrology, 2009, vol. 20 (3), pp. 655-664.

Wessale J.L., et al., "Pharmacology of Endothelin Receptor Antagonists ABT-627, ABT-546, A-182086 and A-192621: Ex Vivo and in Vivo Studies," Clinical Science, 2002, vol. 103 (Suppl. 48), pp. 112S-117S.

Whitworth J.A., et al., "2003 World Health Organization (WHO)/ International Society of Hypertension (ISH) Statement on Management of Hypertension," Journal of Hypertension, 2003, vol. 21 (11), pp. 1983-1992.

Williams B., et al., "Guidelines for Management of Hypertension: Report of the Fourth Working Party of the British Hypertension Society, 2004-BHS IV," Journal of Human Hypertension, 2004, vol. 18 (3), pp. 139-185.

Wu-Wong J.R., et al., "Pharmacology of Endothelin Receptor Antagonists ABT-627, ABT-546, A-182086 and A-192621: in Vitro Studies," Clinical Science, 2002, vol. 103 (Suppl. 48), pp. 107S-111S.

Kohan D.E., "Biology of Endothelin Receptors in the Collecting Duct," Kidney International, 2009, vol. 76 (5), pp. 481-486.

Kohan D.E., et al., "Addition of Atrasentan to Renin-Angiotensin System Blockade Reduces Albuminuria in Diabetic Nephropathy," Journal of the American Society of Nephrology, 2011, vol. 22 (4), pp. 763-772.

Kohan D.E., et al., "Endothelin Antagonists for Diabetic and Non-Diabetic Chronic Kidney Disease," British Journal of Clinical Pharmacology, 2012.

Kowala M.C., et al., "Selective Blockade of the Endothelin Subtype A Receptor Decreases Early Atherosclerosis in Hamsters Fed Cholesterol," American Journal of Pathology, 1995, vol. 146 (4), pp. 819-826.

Lakhdar R., et al., "Safety and Tolerability of Angiotensin-Converting Enzyme Inhibitor Versus the Combination of Angiotensin-Converting Enzyme Inhibitor and Angiotensin Receptor Blocker in Patients with Left Ventricular Dysfunction: A Systematic Review and Meta-Analysis of Randomized Controlled Trials," Journal of Cardiac Failure, 2008, vol. 14 (3), pp. 181-188.

Levin E.R., "Endothelins," New England Journal of Medicine, 1995, vol. 333 (6), pp. 356-363.

Lewis E.J., et al., "Renoprotective Effect of the Angiotensin-Receptor Antagonist Irbesartan in Patients with Nephropathy Due to Type 2 Diabetes," New England Journal of Medicine, 2001, vol. 345 (12), pp. 851-860.

Lip G.Y., "Darusentan (Abbott Laboratories)," IDrugs, 2001, vol. 4 (11), pp. 1284-1292.

Luetscher J.A., et al., "Increased Plasma Inactive Renin in Diabetes Mellitus. A Marker of Microvascular Complications," New England Journal of Medicine, 1985, vol. 312 (22), pp. 1412-1417.

Luscher T.F., et al., "Hemodynamic and Neurohumoral Effects of Selective Endothelin a (et(a)) Receptor Blockade in Chronic Heart Failure: the Heart Failure Et(a) Receptor Blockade Trial (heat)," Circulation, 2002, vol. 106 (21), pp. 2666-2672.

Mackinnon M., et al., "Combination Therapy with an Angiotensin Receptor Blocker and an ACE Inhibitor in Proteinuric Renal Disease: A Systematic Review of the Efficacy and Safety Data," American Journal of Kidney Diseases, 2006, vol. 48 (1), pp. 8-20.

Mann J.F., et al., "Avosentan for Overt Diabetic Nephropathy," Journal of the American Society of Nephrology, 2010, vol. 21 (3), pp. 527-535.

Marre M., et al., "Prevention of Diabetic Nephropathy with Enalapril in Normotensive Diabetics with Microalbuminuria," BMJ, 1988, vol. 297 (6656), pp. 1092-1095.

Messerli F.H., et al., "Of Fads, Fashion, Surrogate Endpoints and Dual RAS Blockade," European Heart Journal, 2010, vol. 31 (18), pp. 2205-2208.

Metabolite [online], [retrieved on Nov. 10, 2009]. Retrieved from the Internet< URL: http://www.answers.com/topic/metabolite>.

Misra S., et al., "ACE inhibitors and ARBs: One or the Other—Not Both—for High-Risk Patients," The Journal of Family Practice, 2009, vol. 58 (1), pp. 24-27.

Mohanan A., et al., "TRC120038, a Novel Dual AT(1)/ET(A) Receptor Blocker for Control of Hypertension, Diabetic Nephropathy, and Cardiomyopathy in ob-ZSF1 Rats," International Journal of Hypertension, vol. 2011, Article ID 751513, 12 pages.

Mylona P., et al., "Update of REACH-1 and MERIT-HF Clinical Trials in Heart Failure. Cardio.net Editorial Team," European Journal of Heart Failure, 1999, vol. 1 (2), pp. 197-200.

Nakamura Y., et al., "Cells Cycle-Dependent Expression of Endothelin Receptors mRNA in Cultured Mesangial Cells," Journal of the American Society of Nephrology, 1991, vol. 2 (3), :410 (abstract).

Nakao N., et al., "Combination Treatment of Angiotensin-II Receptor Blocker and Angiotensin-Converting-Enzyme Inhibitor in Non-Diabetic Renal Disease (COOPERATE): a Randomised Controlled Trial," Lancet, 2003, vol. 361 (9352), pp. 117-124.

Nakov R., et al., "Darusentan: An Effective EndothelinA Receptor Antagonist for Treatment of Hypertension," American Journal of Hypertension, 2002, vol. 15 (7 Pt 1), pp. 583-589.

Non-Final Office Action mailed Jun. 7, 2010 for U.S. Appl. No. 12/196,635, filed Aug. 22, 2008.

Non-Final Office Action mailed Nov. 17, 2009 for U.S. Appl. No. 12/196,635, filed Aug. 22, 2008.

Novartis Pharmaceuticals Corporation, Label for Aliskiren, Mar. 2012, pp. 1-16.

O'Connor C.M., et al., "Tezosentan in Patients with Acute Heart Failure and Acute Coronary Syndromes: Results of the Randomized

(56) References Cited

OTHER PUBLICATIONS

Intravenous TeZosentan Study (RITZ-4)," Journal of the American College of Cardiology, 2003, vol. 41 (9), pp. 1452-1457.
Opgenorth T.J., et al., "Pharmacological Characterization of A-127722: An Orally Active and Highly Potent ETA-Selective Receptor Antagonist," Journal of Pharmacology and Experimental Therapeutics, 1996, vol. 276 (2), pp. 473-481.
Parving H.H., et al., "Cardiorenal End Points in a Trial of Aliskiren for Type 2 Diabetes," New England Journal of Medicine, 2012, vol. 367 (23), pp. 2204-2213.
Parving H.H., et al., Cardiorenal End Points in a Trial of Aliskiren for Type 2 Diabetes, Protocol, New England Journal of Medicine, 2012.
Parving H.H., et al., Cardiorenal End Points in a Trial of Aliskiren for Type 2 Diabetes, Supplementary Appendix, New England Journal of Medicine, 2012.
Parving H.H., et al., "Diabetic Nephropathy", in: The Kidney, 8th Edition, Chapter 36, Brenner B.M., et al., Eds., Saunders Elsevier, 2004, pp. 1265-1298.
Pitt B., et al., "Aldosterone Receptor Antagonists for Heart Failure: Current Status, Future Indications," Cleveland Clinic Journal of Medicine, 2006, vol. 73 (3), pp. 257-260.
Racemate [online], [retrieved on Nov. 10, 2009]. Retrieved from the Internet:< URL: http://www.chemicool.com/definition/racemate.html>.
Raichlin E., et al., "Efficacy and Safety of Atrasentan in Patients with Cardiovascular Risk and Early Atherosclerosis," Hypertension, 2008, vol. 52 (3), pp. 522-528.
Rapoport R.M., et al., "Endothelin(A)-endothelin(B) Receptor Cross Talk in Endothelin-1-Induced Contraction of Smooth Muscle," Journal of Cardiovascular Pharmacology, 2012, vol. 60 (5), pp. 483-494.
Remuzzi G., et al., "New Therapeutics that Antagonize Endothelin: Promises and Frustrations," Nature Reviews Drug Discovery, 2002, vol. 1 (12), pp. 986-1001.
Riechers H., et al., "Discovery and Optimization of a Novel Class of Orally Active Nonpeptidic Endothelin-A Receptor aAntagonists," Journal of Medicinal Chemistry, 1996, vol. 39 (11), pp. 2123-2128.
Sakurai T., et al., "Cloning of a cDNA Encoding a Non-Isopeptide-Selective Subtype of the Endothelin Receptor," Nature, 1990, vol. 348 (6303), pp. 732-735.
Saleh M.A., et al., "Distinct Actions of Endothelin A-Selective Versus Combined Endothelin A/B Receptor Antagonists in Early Diabetic Kidney Disease," Journal of Pharmacology and Experimental Therapeutics, 2011, vol. 338 (1), pp. 263-270.
Saleh M.A., et al., "Endothelin Receptor A-Specific Stimulation of Glomerular Inflammation and Injury in a Streptozotocin-Induced Rat Model of Diabetes," Diabetologia, 2011, vol. 54 (4), pp. 979-988.
Sasser J.M., et al., "Endothelin A Receptor Blockade Reduces Diabetic Renal Injury via an Anti-Inflammatory Mechanism," Journal of the American Society of Nephrology, 2007, vol. 18 (1), pp. 143-154.
Schepkens H., et al., "Life-Threatening Hyperkalemia during Combined Therapy with Angiotensin-Converting Enzyme Inhibitors and Spironolactone: An Analysis of 25 Cases," American Journal of Medicine, 2001, vol. 110 (6), pp. 438-441.
Schiffrin E.L., "Endothelin in Hypertension," Current Opinion in Cardiology, 1995, vol. 10 (5), pp. 485-494.
Shaw S.G., et al., "Endothelin Antagonism Prevents Diabetic Retinopathy in NOD Mice: A Potential Role of the Angiogenic Factor Adrenomedullin," Experimental Biology and Medicine, 2006, vol. 231 (6), pp. 1101-1105.
Shaw S.G., et al., "Insulin Resistance, Obesity and the Metabolic Syndrome. Is there a Therapeutic Role for Endothelin-1 Antagonists?," Current Vascular Pharmacology, 2005, vol. 3 (4), pp. 359-363.
Sorokin A., et al., "Physiology and Pathology of Endothelin-1 in Renal Mesangium," American Journal of Physiology. Renal Physiology, 2003, vol. 285 (4), pp. F579-F589.
Takahashi K., et al., "Elevated Plasma Endothelin in Patients with Diabetes Mellitus," Diabetologia, 1990, vol. 33 (5), pp. 306-310.
Tamirisa P., et al., "Endothelin and Endothelin Antagonism: Roles in Cardiovascular Health and Disease," American Heart Journal, 1995, vol. 130 (3 Pt 1), pp. 601-610.
Taner C.B., et al., "Treatment with Endothelin-Receptor Antagonists Increases NOS Activity in Hypercholesterolemia," Journal of Applied Physiology, 2001, vol. 90 (3), pp. 816-820.
Tautomer [online], [retrieved on Nov. 10, 2009]. Retrieved from the Internet< URL: http://medical-dictionalythefreedictionary.com/tautomer>.
Terada Y., et al., "Cyclin D1, p16, and Retinoblastoma Gene Regulate Mitogenic Signaling of Endothelin in Rat Mesangial Cells," Kidney International, 1998, vol. 53 (1), pp. 76-83.
A Clinical Study to Evaluate the Effects of Darusentan on Safety and Efficacy in Subjects With Resistant Systolic Hypertension Receiving Combination Therapy With Three or More Blood Pressure Lowering Drugs, NCT00364026, Aug. 10, 2006. Retrieved from the Internet:< URL: http://clinicaltrials.gov/ct/show/NCT00364026>.
Albuminuria [online], [retrieved on Jul. 28, 2009]. Retrieved from the Internet:< URL: http://www.medterms.com/script/main/art.asp?articlekey=6851>.
American Diabetes Association, Nephropathy in Diabetes, Diabetes Care, 2004, vol. 27 (Suppl. 1), pp. S79-S83.
Andress D.L., et al., "Clinical Efficacy of the Selective Endothelin A Receptor Antagonist, Atrasentan, in Patients with Diabetes and Chronic Kidney Disease (CKD)," Life Sciences, 2012, vol. 91 (13-14), pp. 739-742.
Arai H., et al., "Cloning and Expression of a cDNA Encoding an Endothelin Receptor," Nature, 1990, vol. 348 (6303), pp. 730-732.
Atkins R.C., et al., "Proteinuria Reduction and Progression to Renal Failure in Patients with Type 2 Diabetes Mellitus and Overt Nephropathy," American Journal of Kidney Diseases, 2005., vol. 45 (2), pp. 281-287.
Babaei S., et al., "Blockade of Endothelin Receptors Markedly Reduces Atherosclerosis in LDL Receptor Deficient Mice: Role of Endothelin in Macrophage Foam Cell Formation," Cardiovascular Research, 2000, vol. 48 (1), pp. 158-167.
Balsiger B., et al., "Endothelin A-Receptor Blockade in Experimental Diabetes Improves Glucose Balance and Gastrointestinal Function," Clinical Science, 2002, vol. 103 (Suppl. 48), pp. 430S-433S.
Banes-Berceli A.K., et al., "Angiotensin Ii and Endothelin-1 Augment the Vascular Complications of Diabetes Via Jak2 Activation," American Journal of Physiology Heart and Circulatory Physiology, 2007, vol. 293 (2), pp. H1291-H299.
Barton M., et al., "Endothelin: 20 years from Discovery to Therapy," Canadian Journal of Physiology and Pharmacology, 2008, vol. 86 (8), pp. 485-498.
Barton M., et al., "Endothelin ETA Receptor Blockade Restores NO-Mediated Endothelial Function and Inhibits Atherosclerosis in Apolipoprotein E-Deficient Mice," Proceedings of the National Academy of Sciences, 1998, vol. 95 (24), pp. 14367-14372.
Barton M., "Reversal of Proteinuric Renal Disease and the Emerging Role of Endothelin," Nature Clinical Practice. Nephrology, 2008, vol. 4 (9), pp. 490-501.
Battistini B., et al., "Profile of Past and Current Clinical Trials Involving Endothelin Receptor Antagonists: the Novel "-sentan" Class of Drug," Experimental Biology and Medicine, 2006, vol. 231 (6), pp. 653-695.
Benigni A., et al., "Renoprotective Effect of Contemporary Blocking of Angiotensin II and Endothelin-1 in Rats with Membranous Nephropathy," Kidney International, 1998, vol. 54 (2), pp. 353-359.
Benigni A., et al., "Unselective Inhibition of Endothelin Receptors Reduces Renal Dysfunction in Experimental Diabetes," Diabetes, 1998, vol. 47 (3), pp. 450-456.
Berthiaume N., et al., "Endothelin Antagonism Improves Hepatic Insulin Sensitivity Associated with Insulin Signaling in Zucker Fatty Rats," Metabolism, 2005, vol. 54 (11), pp. 1515-1523.
Berthiaume N., et al., "Metabolic Responses with Endothelin Antagonism in a Model of Insulin Resistance," Metabolism, 2005, vol. 54 (6), pp. 735-740.
Brenner B.M., et al., "Effects of Losartan on Renal and Cardiovascular Outcomes in Patients with Type 2 Diabetes and Nephropathy," New England Journal of Medicine, 2001, vol. 345 (12), pp. 861-869.

(56) References Cited

OTHER PUBLICATIONS

Chade A.R., et al., "Endothelin-1 Receptor Blockade Prevents Renal Injury in Experimental Hypercholesterolemia," Kidney International, 2003, vol. 64 (3), pp. 962-969.
Chade A.R., et al., "Endothelin-a Receptor Blockade Improves Renal Microvascular Architecture and Function in Experimental Hypercholesterolemia," Journal of the American Society of Nephrology, 2006, vol. 17 (12), pp. 3394-3403.
Chobanian A.V., et al., "Seventh Report of the Joint National Committee on Prevention, Detection, Evaluation, and Treatment of High Blood Pressure," Hypertension, 2003, vol. 42 (6), pp. 1206-1252.
Cosenzi A., et al., "Nephroprotective Effect of Bosentan in Diabetic Rats," Journal of Cardiovascular Pharmacology, 2003, vol. 42 (6), pp. 752-756.
Davenport A.P., et al., "Endothelin ETA and ETB Mrna and Receptors Expressed by Smooth Muscle in the Human Vasculature: Majority of the ETA Sub-type," British Journal of Pharmacology, 1995, vol. 114 (6), pp. 1110-1116.
De Zeeuw D., et al., "Albuminuria, a Therapeutic Target for Cardiovascular Protection in Type 2 Diabetic Patients with Nephropathy," Circulation, 2004, vol. 110 (8), pp. 921-927.
De Zeeuw D., et al., "Proteinuria, a Target for Renoprotection in Patients with Type 2 Diabetic Nephropathy: Lessons from RENAAL," Kidney International, 2004, vol. 65 (6), pp. 2309-2320.
Definition of Derivative and Analog [online], [retrieved on Jul. 7, 2005]. Retrieved from the Internet< URL: http://cancerweb.nci.ac.uk/cgi-bin/omg?query=analog>.
Dhein S., et al., "Long-Term Effects of the Endothelin(A) Receptor Antagonist LU 135252 and the Angiotensin-Converting Enzyme Inhibitor Trandolapril on Diabetic Angiopathy and Nephropathy in a Chronic Type I Diabetes Mellitus Rat Model," Journal of Pharmacology and Experimental Therapeutics, 2000, vol. 293 (2), pp. 351-359.
Ding S.S., et al., "Chronic Endothelin Receptor Blockade Prevents Both Early Hyperfiltration and Late Overt Diabetic Nephropathy in the Rat," Journal of Cardiovascular Pharmacology, 2003, vol. 42 (1), pp. 48-54.
Dislipidemia [online], [retrieved on Jul. 28, 2009]. Retrieved from the Internet< URL: http://www.merck.com/mmpe/sec12/ch159/ch159b.html>.
D'Uscio L.V., et al., "Chronic ET(A) Receptor Blockade Prevents Endothelial Dysfunction of Small Arteries in Apolipoprotein E-deficient Mice," Cardiovascular Research, 2002, vol. 53 (2), pp. 487-495.
Enantiomer [online], [retrieved on Nov. 10, 2009]. Retrieved from the Internet< URL: http://www.chemicool.com/definition/enantiomerhtml>.
European Society of Hypertension-European Society of Cardiology Guidelines Committee, 2003 European Society of Hypertension-European Society of Cardiology Guidelines for the Management of Arterial Hypertension, Journal of Hypertension, 2003, vol. 21 (6), pp. 1011-1053.
Extended European Search Report for Application No. EP12182366, mailed on Dec. 13, 2012, 9 pages.
Ferri C., et al., "Circulating Endothelin-1 Levels in Obese Patients with the Metabolic Syndrome," Experimental and Clinical Endocrinology & Diabetes, 1997, vol. 105 (Suppl. 2), pp. 38-40.
Fukami K., et al., "Novel Therapeutic Targets for Diabetic Nephropathy," Endocrine, Metabolic & Immune Disorders Drug Targets, 2007, vol. 7 (2), pp. 83-92.
Glomerular Filtration Rate [online], [retrieved on Jul. 28, 2009]. Retrieved from the Internet< URL: http://www.nlm.nih.gov/medlineplus/ency/article/007305,htm>.
Goddard J., et al., "Endothelin A Receptor Antagonism and Angiotensin-Converting Enzyme Inhibition are Synergistic Via an Endothelin B Receptor-Mediated and Nitric Oxide-Dependent Mechanism," Journal of the American Society of Nephrology, 2004, vol. 15 (10), pp. 2601-2610.
Gray G.A., et al., "The Endothelin System and its Potential as a Therapeutic Target in Cardiovascular Disease," Pharmacology & Therapeutics, 1996, vol. 72 (2), pp. 109-148.
Han H.K., et al., "Targeted Prodrug Design to Optimize Drug Delivery," AAPS PharmSci, 2000, vol. 2 (1), pp. 1-11.
Hocher B., et al., "Effects of Endothelin Receptor Antagonists on the Progression of Diabetic Nephropathy," Nephron, 2001, vol. 87 (2), pp. 161-169 (Abstract only).
Hofman C., et al., "Endothelin A Antagonist LU-135252 and Trandolapril in the Treatment of the Cohen-Rosenthal Diabetic Hypertensive Rat," Blood Press, 2005, vol. 14 (2), pp. 114-119 (Abstract only).
Honing M.L., et al., "Selective ET(A) Receptor Antagonism with ABT-627 Attenuates all Renal Effects of Endothelin in Humans," Journal of the American Society of Nephrology, 2000, vol. 11 (8), pp. 1498-1504.
http://stockjunction.com/modules.php?name=News&file=print&sid=7332, Aug. 18, 2005.
Hypertension [online], [retrieved on Jul. 28, 2009]. Retrieved from the Internet:< URL: http://www.merck.com/mmpe/sec07/ch071/ch071a.html>.
Ibsen H., et al., "Reduction in Albuminuria Translates to Reduction in Cardiovascular Events in Hypertensive Patients: Losartan Intervention for Endpoint Reduction in Hypertension Study," Hypertension, 2005, vol. 45 (2), pp. 198-202.
Insulin Sensitivity [online], [retrieved on Jul. 28, 2009]. Retrieved from the Internet:< URL: http://www.diabetesnet.com/diabetestreatments/insulin_sensitivity.php>.
Khan Z.A., et al., "Endothelins in Chronic Diabetic Complications," Canadian Journal of Physiology and Pharmacology, 2003, vol. 81 (6), pp. 622-634.
Kohan D.E., "Angiotensin II and Endothelin in Chronic Glomerulonephritis," Kidney International, 1998, vol. 54 (2), pp. 646-647.

\* cited by examiner

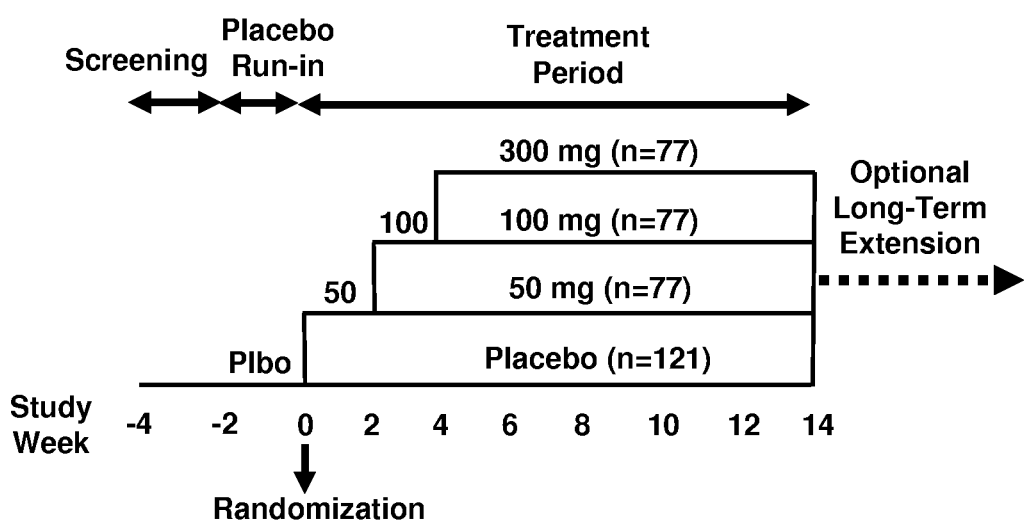

THERAPY FOR COMPLICATIONS OF DIABETES

CROSS-REFERENCE TO RELATED APPLICATIONS

This application is a continuation of U.S. patent application Ser. No. 13/766,266, filed Feb. 13, 2013, which is a continuation of U.S. patent application Ser. No. 12/196,635, filed on Aug. 22, 2008, which claims the benefit of U.S. provisional application Ser. No. 60/957,300, filed on Aug. 22, 2007, the disclosure of each of which is incorporated herein by reference in its entirety.

FIELD OF THE INVENTION

The present invention relates to methods and therapeutic combinations useful for improving clinical outcomes in diabetic patients having complications of diabetes such as diabetic nephropathy and/or metabolic syndrome.

BACKGROUND OF THE INVENTION

Hyperglycemia in diabetes mellitus, if not controlled, over time causes certain irreversible morphologic changes including glomerular fibrosis in kidneys of affected subjects, a condition known as diabetic nephropathy that is associated with decline in renal function, eventually leading to end-stage renal disease. In type 1 (insulin-dependent) diabetes, glycemic control is usually achievable with chronic insulin therapy; however, in type 2 (non-insulin-dependent) diabetes, insulin alone may be ineffective in preventing hyperglycemia. Even in patients with type 1 diabetes, insulin sensitivity can be partially or completely lost. Insulin resistance, or loss of insulin sensitivity, is one of an array of physiological changes that occur in some individuals who are both obese and diabetic; such physiological changes are collectively known as metabolic syndrome. Diabetic nephropathy and metabolic syndrome are serious complications of diabetes that can dramatically reduce quality of life and survival time. A feature of both these complications is arterial hypertension, which superimposes risk of serious cardiac adverse events on the already high risk of chronic kidney failure arising from these complications.

Endothelins (ETs), particularly ET-1, are believed to play a role in mediating the damaging effects of hyperglycemia in the kidney and elsewhere. Expression of ET-1 in endothelial cells of the renal vasculature is upregulated by hyperglycemia; the potent profibrotic action of ET-1 thus generated in the kidney is believed to be involved in the morphologic changes seen in diabetic nephropathy. ET-1 acts via endothelin A ($ET_A$) and endothelin B ($ET_B$) receptors. Elevated plasma ET levels have been reported in patients with diabetes mellitus. See, for example, Takahashi et al. (1990) *Diabetologia* 33:306-310.

Elevated plasma ET levels have also been reported in patients with metabolic syndrome. See Ferri et al. (1997) *Exp. Clin. Endocrinol. Diabetes* 105:38-40. Metabolic syndrome (sometimes referred to as "syndrome X") is characterized by coexistence of glucose intolerance, hypertension, dyslipidemia (specifically elevated LDL (low density lipoprotein) cholesterol and triglycerides and reduced HDL (high density lipoprotein) cholesterol), obesity and susceptibility to cardiovascular disease; these effects are thought to involve a common mechanism in which insulin resistance plays an important part.

The earliest clinical evidence of diabetic nephropathy is microalbuminuria, the appearance of low but abnormal levels (≥30 mg/day) of albumin in the urine. This early stage in development of the disease is known as incipient diabetic nephropathy. Without intervention, about 80% of subjects with type 1 diabetes who develop sustained microalbuminuria exhibit a progressive increase in urinary albumin, eventually (typically after 10-15 years) reaching clinical albuminuria (≥300 mg/day), a stage known as overt diabetic nephropathy. Accompanying the increase in albumin excretion is development of arterial hypertension. In subjects with overt diabetic nephropathy, without intervention, glomerular filtration rate (GFR) gradually falls over a period of 10-20 years, culminating in end-stage renal disease. See American Diabetes Association (2004) *Diabetes Care* 27(suppl. 1):S79-S83. Structural changes in diabetic nephropathy include, in the incipient stage, mesangial expansion and a thickening of the glomerular basement membrane (GBM). An increase in glomerular and kidney size is generally observed. Later, during the overt stage, mesangial nodules and tubular interstitial fibrosis develop.

Hocher et al. (2001) *Nephron* 87:161-169 reported that in rats with streptozotocin-induced diabetes, administration of either the selective $ET_A$ receptor antagonist LU 135252 (darusentan) or the nonselective $ET_A/ET_B$ receptor antagonist LU 224332, in both cases at a dose of 100 mg/kg/day, normalized glomerular matrix protein deposition, indicating an antifibrotic effect. However, neither compound was found to influence serum glucose concentrations in the course of the study.

Dhien et al. (2000) *J. Pharmacol. Exp. Therap.* 293:351-359 reported that LU 135252 at 100 mg/kg/day partially or fully reversed various renal effects of streptozotocin-induced diabetes in rats, including increased glomerular diameter and deposition of eosinophilic material within the glomeruli, but that plasma glucose levels were unaffected by LU 135252.

Sorokin & Kohan (2003) *Am. J. Physiol. Renal Physiol.* 285:F579-F589 remarked that the stage was set for clinical trials of ET inhibitors in patients with glomerular disease characterized by increased ET-1 production and actions.

Avosentan, which may be classified as a selective $ET_A$ or dual $ET_A/ET_B$ receptor antagonist, has been reported to be in Phase III clinical development for diabetic nephropathy. See Battistini et al. (2006) *Exp. Biol. Med.* 231:653-695.

U.S. Pat. No. 6,197,780 to Münter & Kirchengast reported that treatment of obese mice with "substance 23" (darusentan) at 50 mg/kg/day completely prevented increase in body weight. A method is claimed therein for treating a patient having hyperlipidemia, comprising administering a therapeutically effective amount of an ET antagonist (e.g., darusentan) to the patient.

Balsiger et al. (2002) *Clin. Sci.* 103(Suppl. 48):430S-433S reported that in a rat model of type 2 diabetes, BSF 208075 (said to be a selective $ET_A$ receptor antagonist) reduced plasma glucose levels and improved plasma glucose clearance rates in hyperglycemic rats.

On the other hand, Shaw et al. (2006) *Exp. Biol. Med.* 231:1101-1105 reported that in a mouse model of non-obese type 1 diabetes, the selective $ET_A$ receptor antagonist LU 208075 (ambrisentan) did not reduce the elevated plasma glucose levels seen in untreated animals.

According to Berthiaume et al. (2005) *Metab. Clin. Exp.* 54:735-740, some studies have shown desensitization by ET-1 of insulin signaling, leading to a decrease in glucose uptake, while other studies have shown opposite results. A study is reported therein of effects of the selective $ET_A$ receptor antagonist atrasentan in a rat model of insulin resistance.

At a dose of 5 mg/kg/day, atrasentan was reported to significantly reduce 3-hour fasting insulin level but not 3-hour fasting glucose level, and to significantly reduce $\Delta_{AUC}$, a measure of incremental area under the curve induced by a meal tolerance test, for glucose, insulin and glucose-insulin index. These results were said to demonstrate an improvement in glucose tolerance and insulin sensitivity and to suggest that chronic endothelin antagonism may have benefits in treatment of insulin resistance and/or diabetes. It was further reported that $ET_A$ receptor blockade by atrasentan led to an increase rather than a decrease in plasma ET-1 levels.

Shaw & Boden (2005) *Current Vascular Pharmacology* 3:359-363 reviewed evidence on effects of ET-1 and proposed that chronically elevated ET-1 levels may be a cause of insulin resistance and impaired glucose tolerance in early stages of type 2 diabetes, obesity and metabolic syndrome. Recent data were said therein to indicate that combined $ET_A/ET_B$ receptor antagonists may function as effectively as selective $ET_A$ blockers. A need was proposed for prospective trials to assess whether ET-1 antagonists, either alone or in combination, are superior to other more conventional treatments such as insulin sensitizers and to evaluate effects of combined therapies on development of insulin resistance and progression of diabetes.

Subjects having diabetic nephropathy and/or metabolic syndrome represent a particularly challenging subpopulation of diabetic patients, for whom therapies giving improved outcomes with respect to quality of life and survival time, through enhanced glycemic control and/or insulin sensitivity, would represent an important advance in the art.

Recognizing that elevated blood pressure occurs in both diabetic nephropathy and metabolic syndrome, and brings its own attendant risks to quality of life and survival time, an even more challenging patient population comprises subjects having at least one of these complications of diabetes and exhibiting inadequate blood pressure control by standard antihypertensive therapies. Subjects exhibiting resistance to a baseline antihypertensive therapy with one or more drugs include patients having clinically diagnosed resistant hypertension. Resistant hypertension is defined by the Seventh Report of the Joint National Committee on Prevention, Detection, Evaluation, and Treatment of High Blood Pressure (JNC 7; Chobanian et al. (2003) *Hypertension* 42:1206-1252) as a failure to achieve goal blood pressure in patients who are adhering to full doses of an appropriate three-drug regimen that includes a diuretic. Further, resistant hypertension is diagnosed by many physicians on the basis of a patient's resistance to adequate, but less than full, doses of an appropriate three-drug regimen because of the risk or occurrence of adverse events associated with full doses. The terms "adequate" and "full" in the present context are defined hereinbelow.

For patients with serious or compelling conditions such as diabetes and chronic kidney disease, JNC 7 recommends a goal of systolic blood pressure (SBP) <130 mmHg and diastolic blood pressure (DBP) <80 mmHg. Despite intensive, multi-drug therapy, only about 50% of patients with diabetes or chronic kidney disease reach traditional blood pressure goals, with even fewer reaching the more stringent goals now recommended by JNC 7. Thus, resistant hypertension is particularly acute for segments of the population which exhibit complications of diabetes such as diabetic nephropathy or metabolic syndrome.

It should be noted that the British Hypertensive Society (BHD-IV; *J. Human Hypertens.* (2004) 18:139-185), the European Society of Hypertension/European Society of Cardiology (ESH/ESC; *J. Hypertens.* (2003) 21:1011-1053), and the World Health Organization/International Society of Hypertension (WHO/ISH; *J. Hypertens.* (2003) 21:1983-1992) guidelines propose similar but not identical blood pressure goals for diabetic patients.

In a news release dated Aug. 18, 2005 (http://stockjunction.com/modules.php?name=News&file=print&sid=7332), Myogen Inc. reported positive results in a clinical trial (DAR-201) evaluating darusentan in resistant hypertension. Among inclusion criteria for DAR-201 were subjects with diabetes and/or chronic kidney disease with mean systolic blood pressure≥130 mmHg (http://clinicaltrials.gov/ct/show/NCT00364026).

Weber et al. (2006) presented a poster, available at http://www.secinfo.com/dvjdn.vbz.d.htm, posted May 16, 2006, reporting, inter alfa, subject demographics in the DAR-201 study. Of 115 subjects enrolled, 70 had diabetes and/or chronic kidney disease, 55 had diabetes and 29 had chronic kidney disease.

Nakov et al. (2002) *Am. J. Hypertens.* 15:583-589 described a 392-patient study in which moderate hypertension was treated with darusentan at 10 to 100 mg/day. Exclusion criteria included concomitant medication with other antihypertensive drugs. Darusentan was reported to significantly reduce SBP and DBP by comparison with placebo.

German Patent No. DE 19744799 of Knoll mentions, in the abstract thereof, combinations of an endothelin antagonist, such as darusentan, and a diuretic said to show synergistic activity in treatment of hypertension, coronary artery disease, cardiac or renal insufficiency, renal or myocardial ischemia, subarachnoid hemorrhage, Raynaud's disease and peripheral arterial occlusion.

U.S. Pat. No. 6,352,992 to Kirchengast et al. proposes pharmaceutical combination preparations comprising a beta-receptor blocker and an endothelin antagonist for treatment of vasoconstrictive disorders. Among endothelin antagonists mentioned is darusentan.

German Patent No. DE 19743142 of Knoll proposes combinations of an endothelin antagonist, such as darusentan, and a calcium antagonist for treatment of cardiovascular disorders such as pulmonary hypertension and renal and myocardial ischemia.

U.S. Pat. No. 6,329,384 to Munter et al. proposes combinations of endothelin antagonists, such as darusentan, and renin-angiotensin system inhibitors, in particular angiotensin II antagonists and angiotensin converting enzyme (ACE) inhibitors for treatment of vasoconstrictive disorders such as hypertension, heart failure, ischemia or vasospasms.

German Patent No. DE 19743140 of Knoll proposes combinations of an endothelin antagonist, such as darusentan, and a vasodilator for treatment of cardiovascular disorders such as pulmonary hypertension, renal or myocardial ischemia, subarachnoid hemorrhage, Raynaud's disease, and peripheral arterial occlusion.

International Patent Publication No. WO 2004/082637 of Pharmacia proposes combinations of an aldosterone receptor antagonist with an endothelin receptor antagonist and/or an endothelin converting enzyme inhibitor, compositions thereof, and therapeutic methods for use in treatment of pathological conditions such as hypertension, cardiovascular disease and renal dysfunction.

Improved drug therapies for treatment of patients having complications of diabetes such as diabetic nephropathy and/or metabolic syndrome, especially such patients exhibiting resistance to a baseline antihypertensive therapy with one or more drugs, for example patients having clinically diagnosed resistant hypertension, would be highly desirable.

SUMMARY OF THE INVENTION

There is now provided a method for enhancing glycemic control and/or insulin sensitivity in a human subject having diabetic nephropathy and/or metabolic syndrome, comprising administering to the subject a selective endothelin A ($ET_A$) receptor antagonist in a glycemic control and/or insulin sensitivity enhancing effective amount.

There is further provided a method for treating a complex of comorbidities in an elderly diabetic human subject, comprising administering to the subject a selective $ET_A$ receptor antagonist in combination or adjunctive therapy with at least one additional agent that is (i) other than a selective $ET_A$ receptor antagonist and (ii) effective in treatment of diabetes and/or at least one of said comorbidities other than hypertension. Optionally the combination or adjunctive therapy further comprises administration of at least one antihypertensive other than a selective $ET_A$ receptor antagonist.

There is still further provided a therapeutic combination comprising a selective $ET_A$ receptor antagonist and at least one antidiabetic, anti-obesity or antidyslipidemic agent other than a selective $ET_A$ receptor antagonist.

Other embodiments, including particular aspects of the embodiments summarized above, will be evident from the detailed description that follows.

BRIEF DESCRIPTION OF THE DRAWINGS

FIG. 1 is a schematic diagram of the clinical study described in Example 2 herein.

DETAILED DESCRIPTION

The term "diabetic nephropathy" as used herein will be understood to include both incipient and overt stages of diabetic nephropathy, whether diagnosed or not, but most typically as diagnosed by a clinician or physician. The term "metabolic syndrome" as used herein refers to a complex of obesity, hypertension, dyslipidemia and diabetes marked by a degree of insulin resistance. The existence of metabolic syndrome as a true clinical syndrome is not universally accepted; it will be understood that in the present context a patient having metabolic syndrome is one exhibiting a complex of conditions as itemized above, whether or not "metabolic syndrome" is formally diagnosed in the patient.

In one embodiment, the method of the invention is "for enhancing glycemic control and/or insulin sensitivity" in a human subject. Where glycemic control is enhanced, such enhancement can, but does not necessarily, arise from increased insulin sensitivity. Likewise, where insulin sensitivity is enhanced, such enhancement can, but does not necessarily, lead to improved glycemic control.

In one embodiment, practice of the method leads to enhancement of glycemic control, particularly in a subject having diabetic nephropathy and/or metabolic syndrome.

In another embodiment, practice of the method leads to enhancement of insulin sensitivity, particularly in a subject having diabetic nephropathy and/or metabolic syndrome. Insulin sensitivity may be measured by standard insulin models, such as HOMA-IR (homeostasis model assessment of insulin resistance).

In yet another embodiment, practice of the method leads to enhancement in both glycemic control and insulin sensitivity, particularly in a subject having diabetic nephropathy and/or metabolic syndrome.

Enhancement of glycemic control is typically manifested by a reduction in tendency for hyperglycemia. A fasting (e.g., preprandial) blood glucose level greater than about 140 mg/dl, or a bedtime blood glucose level greater than about 160 mg/dl, can be evidence of hyperglycemia. Any reduction in blood glucose level can be beneficial to a subject having hyperglycemia, for example a reduction by at least about 5, at least about 10, at least about 15 or at least about 20 mg/dl. Ideally, glucose level is brought into a goal range for healthy subjects of about 80 to about 120 mg/dl (preprandial) or about 100 to about 140 mg/dl (bedtime). Reduction of glucose level in urine can also provide evidence of enhanced glycemic control, but is less reliable than blood measurements because excretion of glucose in urine typically does not occur unless blood glucose level exceeds about 180 mg/dl.

For some purposes, a superior measure of glycemic control is the glycosylated hemoglobin ($HbA_{1c}$) test. This test reflects blood glucose concentration over a period of time related to the life-span of red blood cells (about 120 days), and consequently is not affected by daily or hourly fluctuations in blood glucose level. A patient having an $HbA_{1c}$ test result greater than about 8% is normally considered hyperglycemic. Any reduction in $HbA_{1c}$ level can be beneficial to such a patient, for example a reduction by at least about 0.5, at least about 1, at least about 1.5 or at least about 2 percentage points. Ideally, $HbA_{1c}$ level is brought into a goal range for healthy subjects of about 4% to about 6%.

Subjects having diabetic nephropathy and/or metabolic syndrome can be of any age, but incidence of these complications of diabetes increases markedly with age. Older subjects can respond differently from younger subjects to treatment, and can have a different spectrum of adverse effects. It is contemplated herein that elderly subjects (i.e., subjects at least about 50, for example at least about 55, at least about 60 or at least about 65 years old) can benefit especially greatly from treatment according to the present method, in part because of the severity with which their quality of life and survival time are impacted by these complications of diabetes, and in part because the particular adverse side effects that have been noted for ET antagonists, including reproductive effects, are of lesser significance later in life.

In one embodiment the subject has incipient diabetic nephropathy.

In another embodiment the subject has overt diabetic nephropathy.

In a further embodiment the subject has incipient or overt diabetic nephropathy and practice of the method provides a further beneficial effect in one or more morphologic markers of diabetic nephropathy. A "morphologic marker" in the present context is any structural or histological feature of the kidney or a tissue thereof, whether observable macroscopically, by light microscopy or by electron microscopy. Such markers can be observable directly, for example by biopsy, or indirectly, through a secondary effect specific to the marker. Examples of morphologic markers of diabetic nephropathy include, without limitation, kidney size, kidney weight, GBM thickening, mesangial expansion, deposition of collagen, fibronectin and laminin, nephron density, nodular glomerulosclerosis, atherosclerosis of renal vasculature or a combination thereof.

In a still further embodiment the subject has incipient or overt diabetic nephropathy and practice of the method provides a further beneficial effect in one or more indicators of renal function, for example GFR, creatinine clearance, albuminuria or a combination thereof.

A "beneficial effect" of the present method can take the form of an improvement over baseline, i.e., an improvement over a measurement or observation made prior to initiation of therapy according to the method. For example, a reduction in amount of collagen deposited, an increase in GFR (in a subject having overt diabetic nephropathy) or a reduction in albuminuria by comparison with a baseline level would represent such an improvement.

A "beneficial effect" can also take the form of an arresting, slowing, retarding or stabilizing of a deleterious progression in any of the above markers or functional effects of diabetic nephropathy. For example, even if GFR is not increased or albuminuria is not reduced by comparison with baseline measurements, a reduction in the rate of decrease of GFR or the rate of increase of albuminuria would represent a beneficial effect of the present method.

Thus in one embodiment, practice of the invention leads to an arresting, slowing, retarding or stabilizing of the progression of diabetic nephropathy in the subject. Such arresting, slowing, retarding or stabilizing of progression of the disease can result in extension of the time to end-stage renal disease or chronic kidney failure, which in turn can extend survival time of the subject.

A selective $ET_A$ receptor antagonist useful herein exhibits an affinity (as expressed by dissociation constant $K_i$) for $ET_A$ not greater than about 10 nM and a selectivity for $ET_A$ over $ET_B$ (as expressed by the ratio $K_i(ET_B)/K_i(ET_A)$) of at least about 50. In various embodiments $K_i(ET_A)$ is not greater than about 5 nM, not greater than about 2 nM, not greater than about 1 nM, not greater than about 0.5 nM or not greater than about 0.2 nM. In various embodiments $K_i(ET_B)/K_i(ET_A)$ is at least about 100, at least about 200, at least about 500 or at least about 1000.

Suitable selective $ET_A$ receptor antagonists can be identified by one of ordinary skill from literature on such antagonists, based on the disclosure herein, but a non-limiting list of such antagonists includes ambrisentan, atrasentan, avosentan, BMS 193884, BQ-123, CI-1020, clazosentan, darusentan, edonentan, S-0139, SB-209670, sitaxsentan, TA-0201, tarasentan, TBC 3711, tezosentan, YM-598, ZD-1611 and ZD-4054, as well as salts, esters, prodrugs, metabolites, tautomers, racemates and enantiomers thereof.

In one embodiment, the selective $ET_A$ receptor antagonist comprises darusentan ((+)-(S)-2-[(4,6-dimethoxy-2-pyrimidinyl)oxy]-3-methoxy-3,3-diphenylpropionic acid). This compound has the formula

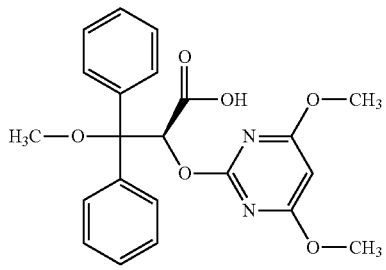

Riechers et al. (1996) *J. Med. Chem.* 39:2123-2128 reported that 2-(4,6-dimethoxypyrimidin-2-yloxy)-3-methoxy-3,3-diphenylpropionic acid in racemic form has $K_i(ET_A)$ of 6 nM and $K_i(ET_B)$ of 371 nM, thus selectivity $K_i(ET_B)/K_i(ET_A)$ for the racemate based on these data can be calculated as about 62. It was further reported therein that the pure enantiomers have an affinity for $ET_A$ of 3 nM and 150 nM. The more potent enantiomer was concluded to be the (S)-enantiomer.

More recently, Lip (2001) *IDrugs* 4(11):1284-1292 reported the (S)-enantiomer (darusentan) as having $K_i(ET_A)$ 1.4 nM and selectivity $K_i(ET_B)/K_i(ET_A)$ about 160.

It has now been found that $K_i(ET_B)/K_i(ET_A)$ for darusentan, when measured in a system that achieves steady-state binding, is much greater than previously reported.

To measure affinities of darusentan for $ET_A$ and $ET_B$ receptors in the same human tissue preparation, [125I]-endothelin-1 receptor binding cold ligand competition curves were performed in human myocardial membranes prepared from failing and non-failing left ventricles, and cold ligand dissociation constants ($K_i$) for $ET_A$ and $ET_B$ receptors were determined by computer modeling. Assay conditions included 10 μM Gpp(NH)p (guanylyl-5'-imidodiphosphate) to eliminate high-affinity agonist binding, 18-point competition curves from 1 pM to 100 μM, and a 4-hour incubation time to achieve steady-state binding. Darusentan was found to have the following properties under these conditions (mean of 8 assays):

$K_i(ET_A)$: 0.178±0.055 nM
$K_i(ET_B)$: 216±85 nM
$K_i(ET_B)/K_i(ET_A)$: 1181±148

According to the present method, the selective $ET_A$ receptor antagonist is administered "in a glycemic control and/or insulin sensitivity enhancing effective amount." What constitutes such an effective amount will depend on the particular selective $ET_A$ receptor antagonist used, on the individual subject, on the dosage form and route of administration used and on other factors, and can be readily determined by one of skill in the art without undue experimentation based on the disclosure herein. Any dose that is effective for enhancing glycemic control and/or insulin sensitivity, up to a maximum that is tolerated by the subject without unacceptable adverse side effects, can be administered. Illustratively for darusentan, such a dose is likely to be about 1 to about 600 mg/day, for example about 5 to about 450 mg/day or about 10 to about 300 mg/day. Higher or lower doses can be useful in specific circumstances. Useful doses of other selective $ET_A$ receptor antagonists are doses that are therapeutically equivalent to such a dose of darusentan.

The desired daily dosage amount can be administered in any suitable number of individual doses, for example four times, three times, twice or once a day. With a dosage form having appropriate controlled release properties, a lower frequency of administration may be possible, for example once every two days, once a week, etc.

In one embodiment, the selective $ET_A$ receptor antagonist is administered according to a therapeutic regimen wherein dose and frequency of administration and duration of therapy are effective to lower blood glucose level by at least about 10 mg/dl and/or to lower $HbA_{1c}$ level by at least about 0.5 percentage points.

In another embodiment, the selective $ET_A$ receptor antagonist is administered according to a therapeutic regimen wherein dose and frequency of administration and duration of therapy are effective to achieve a goal preprandial blood glucose level of about 80 to about 120 mg/dl, a goal bedtime blood glucose level of about 100 to about 140 mg/dl and/or a goal $HbA_{1c}$ level not greater than about 7%.

Benefits of the present method may not be evident immediately upon initiating a therapeutic regimen as described herein. In particular, it can take some time for it to become evident that progression of a complication of diabetes such as diabetic neuropathy has been slowed. It is therefore contemplated that administration of a selective $ET_A$ receptor antagonist will in some cases continue for an extended period of time, typically at least about 1 month, more typically at least about 3 months. Duration of therapy in some embodiments can be at least about 1 year, at least about 5 years, or for as long as needed, which can be lifelong (i.e., from a time of initiation of treatment for substantially the remainder of the patient's life). In one embodiment duration of therapy is from a time of diagnosis of diabetic nephropathy (whether incipient or overt) at least to a time of progression of the diabetic nephropathy into end-stage renal disease. In some situations the method of this embodiment will be successful in preventing progression of the disease to end-stage; in such situations the treatment can be continued indefinitely. For example, administration of the selective $ET_A$ receptor antagonist can continue for as long as a therapeutic benefit is provided thereby and any adverse side effects thereof remain commensurate with the therapeutic benefit.

Selective $ET_A$ receptor antagonists are known to be useful as antihypertensive agents. Thus practice of the present method is likely to provide a benefit not only in glycemic control and/or insulin sensitivity as outlined above, but an additional benefit in lowering blood pressure. As hypertension is an important feature of both diabetic nephropathy and metabolic syndrome, these benefits can be mutually reinforcing.

Any one or more measures of blood pressure can be lowered by a method as described herein, including SBP and/or DBP as determined, for example, by sphygmomanometry. SBP and/or DBP can be measured, for example, in a sitting or ambulatory patient.

A "trough sitting" SBP or DBP is measured at a time point when serum concentration of a drug or drugs administered according to a method of the invention is expected to be at or close to its lowest in a treatment cycle, typically just before administration of a further dose. Illustratively, where the drug or drugs are administered once a day at a particular time, for example around 8 am, trough sitting systolic or diastolic blood pressure can be measured at that time, immediately before the daily administration. It is generally preferred to measure trough sitting SBP or DBP at around the same time of day for each such measurement, to minimize variation due to the natural diurnal blood pressure cycle.

A "24-hour ambulatory" SBP or DBP is an average of measurements taken repeatedly in the course of a 24-hour period, in an ambulatory patient.

A "maximum diurnal" SBP or DBP is a measure of highest SBP or DBP recorded in a 24-hour period, and often reflects the peak of the natural diurnal blood pressure cycle, typically occurring in the morning, for example between about 5 am and about 11 am. Commonly, a second peak occurs in the evening, for example between about 5 pm and 10 pm. Such a bimodal waveform diurnal ABP pattern may be especially characteristic of resistant hypertension.

A common feature of resistant hypertension is a nighttime (defined herein as 2200 to 0600) mean systolic ABP that is less than about 10% lower than the daytime (defined herein as 0600 to 2200) mean systolic ABP. The parameter herein termed "day/night ABP ratio" expressed as a percentage is calculated as (daytime mean−nighttime mean)/daytime mean×100. A diurnal ABP pattern having a day/night ABP ratio of less than about 10% is sometimes referred to as a "non-dipping ABP".

The patient receiving therapy according to a method of the invention can be a patient exhibiting resistance to a baseline antihypertensive therapy with one or more drugs. A "baseline antihypertensive therapy" herein means a therapeutic regimen comprising administration of one or more drugs, not including a selective $ET_A$ receptor antagonist, with an objective (which can be the primary objective or a secondary objective of the regimen) of lowering blood pressure in the patient. Each drug according to the regimen is administered at least at a dose considered by an attending physician to be adequate for treatment of hypertension, taking into account the particular patient's medical condition and tolerance for the drug without unacceptable adverse side-effects. An "adequate" dose as prescribed by the physician can be less than or equal to a full dose of the drug. A "full" dose is the lowest of (a) the highest dose of the drug labeled for a hypertension indication; (b) the highest usual dose of the drug prescribed according to JNC 7, BHD-IV, ESH/ESC or WHO/ISH guidelines; or (c) the highest tolerated dose of the drug in the particular patient.

A baseline antihypertensive therapy illustratively comprises administering one or more diuretics and/or one or more antihypertensive drugs selected from (a) angiotensin converting enzyme inhibitors and angiotensin II receptor blockers, (b) beta-adrenergic receptor blockers, (c) calcium channel blockers, (d) direct vasodilators, (e) alpha-1-adrenergic receptor blockers, (f) central alpha-2-adrenergic receptor agonists and other centrally acting antihypertensive drugs, and (g) aldosterone receptor antagonists. Optionally drugs of still further classes can be included in the baseline therapy.

A patient who is "resistant" to a baseline antihypertensive therapy is one in whom hypertension is failing to respond adequately or at all to the baseline therapy. Typically, the patient receiving the baseline therapy is failing to reach an established blood pressure goal, as set forth for U.S. patients, for example, in JNC 7 or comparable standards in other countries (e.g., BHD-IV, ESH/ESC or WHO/ISH guidelines). Illustratively, the JNC 7 goal in a patient having a complicating condition such as diabetes and/or chronic kidney disease is <130 mmHg SBP and <80 mmHg DBP.

Patients resistant to a baseline antihypertensive therapy, especially such a therapy involving a plurality of drugs, clearly represent a very challenging population for treatment. Typically in such patients, increasing dosages of the baseline therapy are not an option because of resulting adverse side effects; furthermore this approach is often ineffective in providing a desired lowering of blood pressure.

A clinically meaningful lowering of blood pressure can be obtained in such patients by use of a selective $ET_A$ receptor antagonist such as darusentan. A reduction of at least about 3 mmHg in any blood pressure parameter can be considered clinically meaningful.

Accordingly, in one embodiment of the present invention, a method for enhancing glycemic control and/or insulin sensitivity and for lowering blood pressure in a patient exhibiting resistance to a baseline antihypertensive therapy comprises administering to the patient a selective $ET_A$ receptor antagonist, for example darusentan, at a dose and frequency effective to provide a reduction of at least about 3 mmHg in trough sitting SBP and/or DBP, 24-hour ambulatory SBP and/or DBP, and/or maximum diurnal SBP and/or DBP.

In patients exhibiting resistance to a baseline antihypertensive therapy with one or more drugs, administration of darusentan adjunctively with these same drugs is surprisingly well tolerated. Accordingly, in another embodiment of the present invention, a method for enhancing glycemic control and/or insulin sensitivity and for lowering blood pressure in a patient exhibiting resistance to a baseline antihypertensive therapy with one or more drugs comprises administering darusentan to the patient adjunctively with said one or more drugs.

While in certain embodiments the selective $ET_A$ receptor antagonist, for example darusentan, can be administered alone, i.e., in monotherapy, it is contemplated that in most cases combination therapy, for example but not necessarily with one or more drugs of the baseline therapy to which the patient has proved resistant, will be desirable. However, a benefit of the administration of darusentan can be that, at least in some circumstances, it can permit dose reduction, or even elimination, of at least one of the drugs in the baseline therapy.

Particularly when used at a full dose, many baseline antihypertensive therapy drugs can have undesirable, in some cases clinically unacceptable or even dangerous, adverse side effects.

For example, especially at full doses, potassium-sparing diuretic drugs can be associated with increased risk of hyperkalemia and related disorders. Overuse of loop diuretics can cause depletion of sodium resulting in hyponatremia and/or extracellular fluid volume depletion associated with hypotension, reduced GFR, circulatory collapse, and thromboembolic episodes. Further, loop diuretics can cause ototoxicity that results in tinnitus, hearing impairment, deafness and/or vertigo. Thiazide diuretics, similarly to loop diuretics, can have adverse effects related to abnormalities of fluid and electrolyte balance. Such adverse events include extracellular volume depletion, hypotension, hypokalemia, hyponatremia, hypochloremia, metabolic alkalosis, hypomagnesemia, hypercalcemia and hyperuricemia. Thiazide diuretics can also decrease glucose tolerance, and increase plasma levels of LDL cholesterol, total cholesterol, and total triglycerides.

Angiotensin converting enzyme (ACE) inhibitors are associated with cough and increased risk of angioedema. Beta-adrenergic receptor blockers are associated with increased risk of bronchospasm, bradycardia, heart block, excess negative inotropic effect, peripheral arterial insufficiency and sometimes male impotence. Calcium channel blockers are associated with increased risk of lower limb edema. Further information on adverse events associated with antihypertensive drugs can be found, for example, in standard reference works such as Goodman & Gilman's *The Pharmaceutical Basis of Therapeutics,* 13th ed.

In situations such as those outlined immediately above, dose reduction or elimination of a baseline therapy drug permitted by use of darusentan can result in a reduced risk or incidence of adverse events by comparison with the baseline therapy alone without such dose reduction or elimination.

"Adjunctive" administration of darusentan (or other selective $ET_A$ receptor antagonist) in the present context means that the darusentan is administered concomitantly with a baseline hypertensive therapy as defined above, with or without dose reduction of one or more drugs in the baseline therapy. For example, darusentan can be administered adjunctively with an adequate to full dose of each of the drugs in the baseline therapy. In adjunctive therapy, the dose and frequency of darusentan administration is, in one embodiment, effective in combination with the baseline therapy to provide a reduction of at least about 3 mmHg in trough sitting SBP and/or DBP, 24-hour ambulatory SBP and/or DBP, and/or maximum diurnal SBP and/or DBP.

A method of the present invention is especially beneficial where the patient has clinically diagnosed resistant hypertension. By definition herein, in general accordance with JNC 7, such a patient exhibits resistance to an antihypertensive regimen of at least three drugs including a diuretic. In one embodiment, the patient having resistant hypertension exhibits resistance to a baseline antihypertensive therapy that comprises at least the following:

(1) one or more diuretics; and
(2) two or more antihypertensive drugs, selected from at least two of the following classes:
   (a) ACE inhibitors and angiotensin II receptor blockers;
   (b) beta-adrenergic receptor blockers; and
   (c) calcium channel blockers.

In some cases, the patient is resistant to an even more comprehensive baseline therapy, further comprising, for example, one or more direct vasodilators, alpha-1-adrenergic blockers, central alpha-2-adrenergic agonists or other centrally acting antihypertensive drugs, and/or aldosterone receptor antagonists.

While in one embodiment the selective $ET_A$ receptor antagonist is administered orally, the invention is not limited to any route of administration, so long as the route selected results in effective delivery of the drug so that the stated benefits are obtainable. Thus administration of the darusentan can illustratively be parenteral (e.g., intravenous, intraperitoneal, subcutaneous or intradermal), transdermal, transmucosal (e.g., buccal, sublingual or intranasal), intraocular, intrapulmonary (e.g., by inhalation) or rectal. Most conveniently for the majority of patients, however, the selective $ET_A$ receptor antagonist is administered orally, i.e., per os (p.o.). Any suitable orally deliverable dosage form can be used for the selective $ET_A$ receptor antagonist, including without limitation tablets, capsules (solid- or liquid-filled), powders, granules, syrups and other liquids, etc.

Most antihypertensive medicines are suitable for once a day administration, and this is true also of darusentan. Thus, particularly where darusentan is being administered in adjunctive therapy with one or more other antihypertensive drugs, it is generally most convenient to administer the darusentan once a day in a dose as indicated above.

Most typically, where the patient has clinically diagnosed resistant hypertension, the selective $ET_A$ receptor antagonist is administered adjunctively with (1) one or more diuretics; and (2) two or more antihypertensive drugs, selected from (a) ACE inhibitors and angiotensin II receptor blockers; (b) beta-adrenergic receptor blockers; and (c) calcium channel blockers. Each of these diuretic and antihypertensive drugs is typically administered at an adequate to full dose. One of skill in the art can readily identify a suitable dose for any particular diuretic or antihypertensive drug from publicly available information in printed or electronic form, for example on the internet.

Mention of a particular diuretic or antihypertensive drug in the present specification and claims will be understood, except where the context demands otherwise, to include pharmaceutically acceptable salts, esters, prodrugs, metabolites, racemates and enantiomers of the drug, to the extent that such salts, esters, prodrugs, metabolites, racemates or enantiomers exist and are therapeutically effective.

Examples of drugs useful in combination or adjunctive therapy with a selective $ET_A$ receptor antagonist, for example darusentan, or as a component of a baseline antihypertensive therapy are classified and presented in several lists below. Some drugs are active at more than one target; accordingly certain drugs may appear in more than one list. Use of any listed drug in a combination or adjunctive therapy of the invention is contemplated herein, independently of its mode of action.

A suitable diuretic can illustratively be selected from the following list:
Organomercurials
chlormerodrin
chlorothiazide
chlorthalidone meralluride
mercaptomerin sodium
mercumatilin sodium
mercurous chloride
mersalyl
Purines
pamabrom
protheobromine
theobromine
Steroids
canrenone
oleandrin
spironolactone
Sulfonamide Derivatives
acetazolamide
ambuside
azosemide
bumetanide
butazolamide
chloraminophenamide
clofenamide
clopamide
clorexolone
disulfamide
ethoxzolamide
furosemide
mefruside
methazolamide
piretanide
torsemide
tripamide
xipamide
Thiazides and Analogs
althiazide
bendroflumethiazide
benzthiazide
benzylhydrochlorothiazide
buthiazide
chlorthalidone
cyclopenthiazide
cyclothiazide
ethiazide
fenquizone
hydrochlorothiazide
hydroflumethiazide
indapamide
methyclothiazide
metolazone
paraflutizide
polythiazide
quinethazone
teclothiazide
trichlormethiazide
Uracils
aminometradine
Unclassified
amiloride
Biogen BG 9719
chlorazanil
ethacrynic acid
etozolin
isosorbide
Kiowa Hakko KW 3902
mannitol
muzolimine
perhexyline
Sanofi-Aventis SR 121463
ticrynafen
triamterene
urea In some embodiments, the diuretic if present comprises a thiazide or loop diuretic. Thiazide diuretics are generally not preferred where the patient has a complicating condition such as diabetes or chronic kidney disease, and in such situations a loop diuretic can be a better choice.

Particularly suitable thiazide diuretics, for example for use with darusentan, include chlorothiazide, chlorthalidone, hydrochlorothiazide, indapamide, metolazone, polythiazide and combinations thereof. Particularly suitable loop diuretics include bumetanide, furosemide, torsemide and combinations thereof.

A suitable ACE inhibitor can illustratively be selected from the following list:
alacepril
benazepril
captopril
ceronapril
cilazapril
delapril
enalapril
enalaprilat
eosinopril
fosinopril
imidapril
lisinopril
moexipril
moveltipril
omapatrilat
perindopril
quinapril
ramipril
sampatrilat
spirapril
temocapril
trandolapril Particularly suitable ACE inhibitors, for example for use with darusentan, include benazepril, captopril, enalapril, fosinopril, lisinopril, moexipril, perindopril, quinapril, ramipril, trandolapril and combinations thereof.

A suitable angiotensin II receptor blocker can illustratively be selected from the following list:
candesartan
eprosartan
irbesartan
losartan
olmesartan
tasosartan
telmisartan
valsartan A suitable beta-adrenergic receptor blocker can illustratively be selected from the following list:
AC 623
acebutolol
alprenolol
atenolol
amosulalol
arotinolol
atenolol
befunolol
betaxolol
bevantolol
bisoprolol
bopindolol
bucindolol bucumolol
bufetolol
bufuralol
bunitrolol
bupranolol
butidrine hydrochloride
butofilolol
carazolol
carteolol
carvedilol
celiprolol
cetamolol
cloranolol
dilevalol
esmolol
indenolol
labetalol
landiolol
levobunolol
mepindolol
metipranolol
metoprolol
moprolol
nadolol
nadoxolol
nebivolol
nifenalol
nipradilol
oxprenolol
penbutolol
pindolol
practolol
pronethalol
propranolol
sotalol
sulfinalol
talinolol
tertatolol
tilisolol
timolol
toliprolol
xibenolol Particularly suitable beta-adrenergic receptor blockers, for example for use with darusentan, include acebutolol, atenolol, betaxolol, bisoprolol, carvedilol, labetalol, metoprolol, nadolol, penbutolol, pindolol, propranolol, timolol and combinations thereof.

A suitable calcium channel blocker can illustratively be selected from the following list:
Arylalkylamines
bepridil
clentiazem
diltiazem
fendiline
gallopamil
mibefradil
prenylamine
semotiadil
terodiline
verapamil
Dihydropyridine Derivatives
amlodipine
aranidipine
barnidipine
benidipine
cilnidipine
efonidipine
elgodipine
felodipine
isradipine
lacidipine
lercanidipine
manidipine
nicardipine
nifedipine
nilvadipine
nimodipine
nisoldipine
nitrendipine
NZ 105
Piperazine Derivatives
cinnarizine
dotarizine
flunarizine
lidoflazine
lomerizine
Unclassified
bencyclane
etafenone
fantofarone
monatepil
perhexyline Particularly suitable calcium channel blockers, for example for use with darusentan, include amlodipine, diltiazem, felodipine, isradipine, nicardipine, nifedipine, nisoldipine, verapamil and combinations thereof.

Optionally, one or more additional antihypertensive drugs can be administered. These can be selected, for example, from direct vasodilators, alpha-1-adrenergic receptor blockers, central alpha-2-adrenergic receptor agonists and other centrally acting antihypertensive drugs, and aldosterone receptor antagonists.

A suitable direct vasodilator can illustratively be selected from the following list:
amotriphene
benfurodil hemisuccinate
benziodarone
chloracizine
chromonar
clobenfurol
clonitrate
cloricromen
dilazep
droprenilamine
efloxate
erythrityl tetranitrate
etafenone
fendiline
hexestrol bis(β-diethylaminoethyl ether)
hexobendine
hydralazine
isosorbide dinitrate
isosorbide mononitrate
itramin tosylate
khellin
lidoflazine
mannitol hexanitrate
minoxidil
nitroglycerin
pentaerythritol tetranitrate
pentrinitrol
perhexyline
pimethylline
prenylamine propatyl nitrate
trapidil
tricromyl
trimetazidine
trolnitrate phosphate
visnadine Particularly suitable direct vasodilators, for example for use with darusentan, include hydralazine, minoxidil and combinations thereof.

A suitable alpha-1-adrenergic receptor blocker can illustratively be selected from the following list:
amosulalol
arotinolol
carvedilol
dapiprazole
doxazosin
ergoloid mesylates
fenspiride
idazoxan
indoramin
labetalol
methyldopa
monatepil
naftopidil
nicergoline
prazosin
tamsulosin
terazosin
tolazoline
trimazosin
yohimbine Particularly suitable alpha-1-adrenergic receptor blockers, for example for use with darusentan, include carvedilol, doxazosin, labetalol, prazosin, terazosin and combinations thereof. It is noted that, of these, carvedilol and labetalol also function as beta-adrenergic receptor blockers.

A suitable central alpha-2-adrenergic receptor agonist or other centrally acting antihypertensive drug can illustratively be selected from the following list:
clonidine
guanabenz
guanadrel
guanfacine
methyldopa
moxonidine
reserpine A suitable aldosterone receptor antagonist can illustratively be selected from the following list:
canrenone
eplerenone
spironolactone Still further classes of drugs that can be useful in combination or adjunctive therapy with darusentan or in a baseline antihypertensive therapy include vasopeptidase inhibitors, NEP (neutral endopeptidase) inhibitors, prostanoids (particularly oral prostanoids), PDE5 (phosphodiesterase type 5) inhibitors, nitrosylated compounds and oral nitrates.

Illustrative vasopeptidase inhibitors include:
fasidotril
omapatrilat
sampatrilat Illustrative NEP inhibitors, some of which are also ACE inhibitors, include:
candoxatril
CGS 26582
MDL 100173
omapatrilat
phosphoramidon
sinorphan
thiorphan
Z13752A Illustrative prostanoids include:
beraprost
cicaprost
epoprostenol
iloprost
$PGE_1$
$PGI_2$ (pro stacyclin)
NS-304
treprostinil Illustrative PDE5 inhibitors include:
sildenafil
tadalafil
vardenafil Other drugs that can be useful in combination or adjunctive therapy with darusentan or in a baseline antihypertensive therapy can illustratively be selected from the following unclassified list:
ajmaline
alfuzosin
Alteon ALT 711
γ-aminobutyric acid
atrial natriuretic peptide
azelnidipine
bethanidine
bietaserpine
bosentan
budralazine
bufeniode
bunazosin
cadralazine
carmoxirole
CD 3400
chlorisondamine chloride
cicletanine
ciclosidomine
clevidipine
debrisoquin
denitronipradilol
desacetylalacepril
deserpidine
diazoxide
dihydralazine
endralazine
fenoldopam
flosequinan
guanethidine
guanidine, N-cyano-N'-4-pyridinyl-N''-(1,2,2-trimethylpropyl)-, monohydrate
guanoxabenz
guanoxan
hexamethonium
ketanserin
LBI 45
levcromakalim
lofexidine
magnesiocard
mebutamate
mecamylamine
normopresil
2-oxazolamine, N-(dicyclopropylmethyl)-4,5-dihydro-, (2E)-2-butenedioate
pargyline
pempidine pentamethonium bromide
pentolinium tartrate
pheniprazine
phentolamine
pildralazine
pinacidil
piperoxan
protoveratrines
3,5-pyridinedicarboxylic acid, 1,4-dihydro-2,6-dimethyl-4-(3-nitrophenyl)-, methyl 1-(phenylmethyl)-3-pyrrolidinyl ester
raubasine
rescimetol
rescinnamine
rilmenidine
saralasin
sodium niroprusside
syrosingopine
Takeda TAK 536
TBC 3711
tetrahydrolipstatin
1,4-thiazepine-4(5H)-acetic acid, 6-[[1-(ethoxycarbonyl)-3-phenylpropyl]amino]-tetrahydro-5-oxo-2-(2-thienyl)
tiamenidine
todralazine
tolonidine
trimethaphan camsylate
tyrosinase
urapidil
zofenopril In one embodiment, the selective $ET_A$ receptor antagonist, more specifically darusentan, is administered concomitantly (e.g., in combination or adjunctive therapy) with one or more of (a) a diuretic selected from the group consisting of chlorothiazide, chlorthalidone, hydrochlorothiazide, indapamide, metolazone, polythiazide, bumetanide, furosemide, torsemide and combinations thereof;

(b) an ACE inhibitor selected from the group consisting of benazepril, captopril, enalapril, fosinopril, lisinopril, moexipril, perindopril, quinapril, ramipril, trandolapril and combinations thereof, and/or an angiotensin II receptor blocker selected from the group consisting of candesartan, eprosartan, irbesartan, losartan, olmesartan, tasosartan, telmisartan, valsartan and combinations thereof;

(c) a beta-adrenergic receptor blocker selected from the group consisting of acebutolol, atenolol, betaxolol, bisoprolol, carvedilol, labetalol, metoprolol, nadolol, penbutolol, pindolol, propranolol, timolol and combinations thereof;

(d) a calcium channel blocker selected from the group consisting of amlodipine, diltiazem, felodipine, isradipine, nicardipine, nifedipine, nisoldipine, verapamil and combinations thereof;

(e) a direct vasodilator selected from the group consisting of hydralazine, minoxidil and combinations thereof;

(f) an alpha-1-adrenergic receptor blocker selected from the group consisting of carvedilol, doxazosin, labetalol, prazosin, terazosin and combinations thereof;

(g) a central alpha-2-adrenergic receptor agonist or other centrally acting drug selected from the group consisting of clonidine, guanabenz, guanadrel, guanfacine, methyldopa, moxonidine, reserpine and combinations thereof; and (h) an aldosterone receptor antagonist selected from the group consisting of canrenone, eplerenone, spironolactone and combinations thereof.

More particularly, the selective $ET_A$ receptor antagonist, more specifically darusentan, can be administered in combination or adjunctive therapy with one or more of (a), (b), (c) and (d) above, optionally further with one or more of (e), (f), (g) and (h).

Still more particularly, the selective $ET_A$ receptor antagonist, more specifically darusentan, can be administered in combination or adjunctive therapy at least with (a) and any two of (b), (c) and (d).

As in the case of the selective $ET_A$ receptor antagonist, the one or more drugs constituting the baseline antihypertensive therapy and optionally administered in combination with the selective $ET_A$ receptor antagonist can be delivered by any suitable route of administration. Generally, such drugs are suitable for oral administration, and many are suitable for once a day oral administration. Thus in one embodiment at least one of the diuretic or antihypertensive drugs in the baseline therapy is orally administered once a day. In a particular embodiment, all drugs in the baseline therapy are orally administered once a day. According to this embodiment, it will generally be found convenient to administer all drugs in the regimen, i.e., the selective $ET_A$ receptor antagonist as well as the baseline therapy drugs, orally once a day.

Fixed-dose combinations of two or more drugs can be achieved in many cases by coformulation of the drugs in a single dosage unit such as a tablet or capsule. For example, coformulations of various drugs useful in a baseline antihypertensive therapy as defined herein are available, including:

amiloride+hydrochlorothiazide;
amlodipine+benazepril;
atenolol+chlorthalidone;
benazepril+hydrochlorothiazide;
bisoprolol+hydrochlorothiazide;
candesartan+hydrochlorothiazide;
captopril+hydrochlorothiazide;
enalapril+felodipine;
enalapril+hydrochlorothiazide;
eprosartan+hydrochlorothiazide;
fosinopril+hydrochlorothiazide;
irbesartan+hydrochlorothiazide;
lisinopril+hydrochlorothiazide;
losartan+hydrochlorothiazide;
methyldopa+hydrochlorothiazide;
metoprolol+hydrochlorothiazide;
moexipril+hydrochlorothiazide;
nadolol+hydrochlorothiazide;
olmesartan+hydrochlorothiazide;
propranolol+hydrochlorothiazide;
quinapril+hydrochlorothiazide;
reserpine+chlorothiazide;
reserpine+chlorthalidone;
reserpine+hydrochlorothiazide;
spironolactone+hydrochlorothiazide;
telmisartan+hydrochlorothiazide;
timolol+hydrochlorothiazide;
trandolapril+verapamil;
triamterene+hydrochlorothiazide; and
valsartan+hydrochlorothiazide.

It will be understood that combination or adjunctive therapies as indicated above, while of particular benefit in patients having resistant hypertension, are not limited to such patients. Hypertension (whether resistant or not) is a common feature of most complications of diabetes, including both diabetic nephropathy and metabolic syndrome, and it is contemplated that combination or adjunctive therapies of a selective $ET_A$ receptor antagonist with one or more antihypertensive drugs other than selective $ET_A$ receptor antagonists can be useful in many diabetic patients having these complications.

Another kind of combination or adjunctive therapy that can be useful according to the present invention includes a selective $ET_A$ receptor antagonist and one or more additional antidiabetic agents other than selective $ET_A$ receptor antagonists. Such additional antidiabetic agents can, for example, be selected from alpha-glucosidase inhibitors, biguanides, exendins, hormones and analogs thereof, meglitinides, sulfonylurea derivatives and thiazolidinediones.

A suitable antidiabetic can illustratively be selected from the following list:
Biguanides
buformin
metformin
phenformin
Hormones and Analogs Thereof
amylin
insulin
insulin aspart
insulin detemir
insulin glargine
insulin glulisine
insulin lispro
liraglutide
pramlintide
Sulfonylurea Derivatives
acetohexamide
carbutamide
chlorpropamide
glibornuride
gliclazide
glimepiride
glipizide
gliquidone
glisoxepid
glyburide
glybuthiazole
glybuzole
glyhexamide
glymidine
tolazamide
tolbutamide
tolcyclamide
Thiazolidinediones
pioglitazone
rosiglitazone
troglitazone
Unclassified
acarbose
exenatide
miglitol
mitiglinide
muraglitazar
nateglinide
repaglinide
sitagliptin
tesaglitazar
vildagliptin
voglibose Particularly suitable antidiabetics, for example for use with darusentan, include acarbose, exenatide, glimepiride, insulins, metformin, nateglinide, pioglitazone, pramlintide, rosiglitazone and combinations thereof.

For a subject with metabolic syndrome, a selective $ET_A$ receptor antagonist can be administered in combination or adjunctive therapy with one or more additional agents selected from antidiabetics (for example as listed above), antihypertensives (for example as listed above), anti-obesity agents and antidyslipidemics.

Suitable anti-obesity agents include anorexics, CB1 receptor blockers and lipase inhibitors.

A suitable anti-obesity agent can illustratively be selected from the following list:
aminorex
amphetamine
benzphetamine
chlorphentermine
clobenzorex
clortermine
cyclexedrine
dextroamphetamine
diethylpropion
N-ethylamphetamine
fenbutrazate
fenfluramine
fenproporex
levophacetoperane
mazindol
mefenorex
methamphetamine
norpseudoephedrine
orlistat
pentorex
phendimetrazine
phenmetrazine
phentermine
phenylpropanolamine
rimonabant
sibutramine Particularly suitable anti-obesity agents, for example for use with darusentan, include benzphetamine, methamphetamine, orlistat, phendimetrazine, phentermine, rimonabant, sibutramine and combinations thereof.

Suitable antidyslipidemics include bile acid sequestrants, cholesterol absorption inhibitors, fibrates, HMG CoA reductase inhibitors (statins), nicotinic acid derivatives, and thyroid hormones and analogs thereof.

A suitable antidyslipidemic can illustratively be selected from the following list:
Bile Acid Sequestrants
cholestyramine resin
colesevelam
colestilan
colestipol
polidexide
Fibrates
bezafibrate
binifibrate
ciprofibrate
clinofibrate
clofibrate
clofibric acid
etofibrate
fenofibrate
gemfibrozil
pirifibrate
ronifibrate
simfibrate
theofibrate HMG CoA Reductase Inhibitors
atorvastatin
cerivastatin
fluvastatin
lovastatin
pitavastatin
pravastatin
rosuvastatin
simvastatin
Nicotinic Acid Derivatives
acipimox
aluminum nicotinate
niacin (nicotinic acid)
niceritrol
oxiniacic acid
Thyroid Hormones and Analogs Thereof
dextrothyroxine
etiroxate
thyropropic acid
Unclassified
acifran
avasimibe
benfluorex
detaxtran
eicosapentaenoic acid
ezetimibe
meglutol
melinamide
omega-3 acid ethyl esters
γ-oryzanol
pantethine
pirozadil
policonasol
probucol
β-sitosterol
sultosilic acid
tiadenol
torcetrapib
xenbucin Particularly suitable antidyslipidemics, for example for use with darusentan, include atorvastatin, colesevelam, ezetimibe, fenofibrate, fluvastatin, lovastatin, niacin, rosuvastatin, simvastatin and combinations thereof.

It is further contemplated that the selective $ET_A$ receptor antagonist can itself have useful antidyslipidemic activity, for example secondary to its activity in enhancing glycemic control and/or insulin sensitivity.

When a selective $ET_A$ receptor antagonist is used in adjunctive therapy with one or more additional antidiabetics, antihypertensives, anti-obesity agents and/or antidyslipidemics, the selective $ET_A$ receptor antagonist and at least one additional antidiabetic, antihypertensive, anti-obesity agent and/or antidyslipidemic can be administered at different times or at about the same time (at exactly the same time or directly one after the other in any order). The selective $ET_A$ receptor antagonist and the at least one antidiabetic, antihypertensive, anti-obesity agent and/or antidyslipidemic can be formulated in one dosage form as a fixed-dose combination for administration at the same time, or in two or more separate dosage forms for administration at the same or different times.

Separate dosage forms can optionally be co-packaged, for example in a single container or in a plurality of containers within a single outer package, or co-presented in separate packaging ("common presentation"). As an example of co-packaging or common presentation, a kit is contemplated comprising, in separate containers, darusentan and at least one drug useful in combination or adjunctive therapy with darusentan, for example an antidiabetic, antihypertensive, anti-obesity agent or antidyslipidemic. In another example, darusentan and at least one drug useful in combination or adjunctive therapy with darusentan, for example an antidiabetic, antihypertensive, anti-obesity agent or antidyslipidemic, are separately packaged and available for sale independently of one another, but are co-marketed or co-promoted for use according to the invention. The separate dosage forms can also be presented to a patient separately and independently, for use according to the invention.

A further embodiment of the present invention provides a method for treating a complex of comorbidities in an elderly diabetic human subject. This method comprises administering to the subject a selective $ET_A$ receptor antagonist in combination or adjunctive therapy with
(a) at least one additional agent that is (i) other than a selective $ET_A$ receptor antagonist and (ii) effective in treatment of diabetes and/or at least one of said comorbidities other than hypertension, and optionally
(b) at least one antihypertensive other than a selective $ET_A$ receptor antagonist.

An "elderly" subject is as defined hereinabove.

A "comorbidity" is a disease condition present in the subject in addition to diabetes, that adds to the deleterious effects of the diabetes on the subject and/or affects the choice of therapy. Comorbidities can arise secondarily from the diabetes or from other comorbidities, or may arise independently. Among comorbidities commonly occurring in an elderly diabetic patient population are, illustratively, insulin resistance, chronic kidney disease, hypertension, dyslipidemia, obesity, cardiac insufficiency and sleep apnea.

A "complex" of comorbidities is defined herein as the presence of at least two such comorbidities, in addition to the underlying diabetes. In some embodiments the subject presents with at least three, or even four or more, such comorbidities. For example, in metabolic syndrome, a subject can exhibit diabetes with insulin resistance, hypertension, dyslipidemia and obesity.

"Treating" in the present context includes alleviating symptoms, enhancing glycemic control and/or insulin sensitivity, arresting, slowing, retarding or stabilizing progression of a condition or a physiological or morphological marker thereof, and/or improving clinical outcome, for example as measured by quality of life, incidence or severity of adverse cardiac events, time to end-stage renal disease or survival time.

The selective $ET_A$ receptor antagonist can illustratively be selected from those mentioned hereinabove. In one embodiment the selective $ET_A$ receptor antagonist comprises darusentan, for example at dosage amounts and frequencies of administration, by routes of administration and dosage forms, and for duration of treatment as indicated hereinabove.

Several of the comorbidities mentioned above as occurring in elderly diabetic patients have been individually reported in the literature (including literature cited herein) to be mediated by ET-1 and/or to be treatable with a selective $ET_A$ receptor antagonist. However, it has not hitherto been proposed to simultaneously address a complex of comorbidities of diabetes in an elderly patient by treatment with a selective $ET_A$ receptor antagonist such as darusentan; nor has it been proposed to combine such treatment, in adjunctive or combination therapy, with one or more additional agents effective in treatment of diabetes and/or at least one of said comorbidities other than hypertension. Given the spectrum of effects of selective $ET_A$ receptor antagonists but without being bound by theory, it is believed that the selective $ET_A$ receptor antagonist (e.g., darusentan) component of such adjunctive or combination therapy can contribute in a substantial way to clinical improvement in each of a plurality of comorbidities, for example supplementing the effect of, co-acting with, or permitting dose reduction (with potential benefits in reducing adverse side-effects) in at least one additional agent. However, even without such contribution by the selective $ET_A$ receptor antagonist to more than one comorbidity, the adjunctive or combination therapy of the present embodiment brings great benefit to the elderly diabetic patient by enabling a complex of comorbidities, as seen for example in diabetic nephropathy or metabolic syndrome, to be simultaneously addressed.

The at least one additional agent that is (i) other than a selective $ET_A$ receptor antagonist and (ii) effective in treatment of diabetes and/or at least one comorbidity other than hypertension can comprise, for example, one or more antidiabetics, anti-obesity agents and/or antidyslipidemics, including any such agents listed hereinabove. For example, one or more agents selected from acarbose, exenatide, glimepiride, insulins, metformin, nateglinide, pioglitazone, pramlintide, rosiglitazone, benzphetamine, methamphetamine, orlistat, phendimetrazine, phentermine, rimonabant, sibutramine, atorvastatin, colesevelam, ezetimibe, fenofibrate, fluvastatin, lovastatin, niacin, rosuvastatin, simvastatin and combinations thereof can be administered in adjunctive or combination therapy with a selective $ET_A$ receptor antagonist, for example darusentan.

Antihypertensive(s) optionally additionally present in the adjunctive or combination therapy can comprise, for example, agents of any class listed hereinabove, including diuretics, ACE inhibitors, angiotensin II receptor blockers, beta-adrenergic receptor blockers, calcium channel blockers, direct vasodilators, alpha-1-adrenergic receptor blockers, central alpha-2-adrenergic receptor agonists and other centrally acting antihypertensive drugs, aldosterone receptor antagonists, vasopeptidase inhibitors, NEP inhibitors, prostanoids, PDE5 inhibitors, nitrosylated compounds, oral nitrates and renin inhibitors, or combinations of agents from one or more than one such class. For example, where the subject has clinically diagnosed resistant hypertension as one of the comorbidities, the adjunctive or combination therapy can comprise administration of at least one diuretic and at least two antihypertensives selected from at least two of (a) ACE inhibitors and angiotensin II receptor blockers, (b) beta-adrenergic receptor blockers and (c) calcium channel blockers.

Illustratively antihypertensives for use in the method of the present embodiment can be selected from chlorothiazide, chlorthalidone, hydrochlorothiazide, indapamide, metolazone, polythiazide, bumetanide, furosemide, torsemide, benazepril, captopril, enalapril, fosinopril, lisinopril, moexipril, perindopril, quinapril, ramipril, trandolapril, candesartan, eprosartan, irbesartan, losartan, olmesartan, tasosartan, telmisartan, valsartan, acebutolol, atenolol, betaxolol, bisoprolol, carvedilol, labetalol, metoprolol, nadolol, penbutolol, pindolol, propranolol, timolol, amlodipine, diltiazem, felodipine, isradipine, nicardipine, nifedipine, nisoldipine, verapamil and combinations thereof.

A still further embodiment of the present invention provides a therapeutic combination comprising a selective $ET_A$ receptor antagonist and at least one antidiabetic, anti-obesity or antidyslipidemic agent other than a selective $ET_A$ receptor antagonist. Such a combination can have utility in a number of situations, not limited to methods described herein. However, a combination of this embodiment can be especially useful for treating a complex of comorbidities in an elderly diabetic human subject as described above.

The selective $ET_A$ receptor antagonist and the at least one antidiabetic, anti-obesity or antidyslipidemic agent can be present in the combination in two or more separate dosage forms, permitting administration at the same or different times. Such separate dosage forms can be formulated with one or more pharmaceutically acceptable excipients for administration via the same or different routes. In a particular embodiment all agents in the combination are formulated for oral administration; in an even more particular embodiment all agents are formulated for once-daily oral administration and can be administered at the same time each day. Where a treatment regimen includes administration of a plurality of drugs, as in the present instance, there are great benefits in convenience and compliance in standardizing route, frequency and timing of administration in this way.

As indicated hereinabove, separate dosage forms can optionally be co-packaged, for example in a single container or in a plurality of containers within a single outer package, or co-presented in separate packaging, for example as a kit comprising, in separate containers, a selective $ET_A$ receptor antagonist and at least one antidiabetic, anti-obesity or antidyslipidemic agent. The kit can optionally comprise separate labeling information for each agent, or a single product label having information on the therapeutic combination as a whole. In another example, the selective $ET_A$ receptor antagonist and the at least one antidiabetic, anti-obesity or antidyslipidemic agent are separately packaged and available for sale independently of one another, but are co-marketed or co-promoted for use according to the invention. The separate dosage forms can also be presented to a patient separately and independently, for use according to the invention.

In another embodiment, the selective $ET_A$ receptor antagonist and the at least one antidiabetic, anti-obesity or antidyslipidemic agent are coformulated with one or more pharmaceutically acceptable excipients in a single pharmaceutical composition as a fixed-dose combination.

A pharmaceutical composition comprising the selective $ET_A$ receptor antagonist, the at least one antidiabetic, anti-obesity or antidyslipidemic agent, and one or more pharmaceutically acceptable excipients is itself a still further embodiment of the present invention.

In a therapeutic combination or pharmaceutical composition of the invention, the selective $ET_A$ receptor antagonist can illustratively be selected from those mentioned hereinabove. In one embodiment the selective $ET_A$ receptor antagonist comprises darusentan, for example in a dosage amount as set forth hereinabove.

The combination or composition can comprise at least one antidiabetic, for example selected from alpha-glucosidase inhibitors, biguanides, exendins, hormones and analogs thereof, meglitinides, sulfonylurea derivatives and thiazolidinediones. In a particular embodiment the selective $ET_A$ receptor antagonist comprises darusentan and the at least one antidiabetic is selected from acarbose, exenatide, glimepiride, insulins, metformin, nateglinide, pioglitazone, pramlintide, rosiglitazone and combinations thereof.

The combination or composition can comprise at least one anti-obesity agent, for example selected from anorexics, CB1 receptor blockers and lipase inhibitors. In a particular embodiment the selective $ET_A$ receptor antagonist comprises darusentan and the at least one anti-obesity agent is selected from benzphetamine, methamphetamine, orlistat, phendimetrazine, phentermine, rimonabant, sibutramine and combinations thereof.

The combination or composition can comprise at least one antidyslipidemic, for example selected from bile acid sequestrants, cholesterol absorption inhibitors, fibrates, HMG CoA reductase inhibitors, nicotinic acid derivatives, and thyroid hormones and analogs thereof. In a particular embodiment the selective $ET_A$ receptor antagonist comprises darusentan and the at least one antidyslipidemic is selected from atorvastatin, colesevelam, ezetimibe, fenofibrate, fluvastatin, lovastatin, niacin, rosuvastatin, simvastatin and combinations thereof. For example, the combination or composition can comprise a selective $ET_A$ receptor antagonist such as darusentan, a cholesterol absorption inhibitor such as ezetimibe, and an HMG CoA reductase inhibitor (statin) such as atorvastatin, fluvastatin, lovastatin, rosuvastatin or simvastatin.

The combination or composition comprises, in one embodiment, a selective $ET_A$ receptor antagonist, at least one antidiabetic and at least one anti-obesity agent.

The combination or composition comprises, in another embodiment, a selective $ET_A$ receptor antagonist, at least one antidiabetic and at least one antidyslipidemic.

The combination or composition comprises, in yet another embodiment, a selective $ET_A$ receptor antagonist, at least one anti-obesity agent and at least one antidyslipidemic.

The combination or composition comprises, in a still further embodiment, a selective $ET_A$ receptor antagonist, at least one antidiabetic, at least one anti-obesity agent and at least one antidyslipidemic.

According to any embodiment mentioned above, the combination or composition optionally further comprises at least one antihypertensive. The at least one antihypertensive can comprise, for example, one or more agents of any class listed hereinabove or a combination of agents from more than one such class.

An illustrative combination or composition of the invention comprises:
  (a) darusentan as a selective $ET_A$ receptor antagonist;
  (b) one or more of:
    (i) at least one antidiabetic selected from acarbose, exenatide, glimepiride, insulins, metformin, nateglinide, pioglitazone, pramlintide, rosiglitazone and combinations thereof;
    (ii) at least one anti-obesity agent selected from benzphetamine, methamphetamine, orlistat, phendimetrazine, phentermine, rimonabant, sibutramine and combinations thereof; and/or
    (iii) at least one antidyslipidemic selected from atorvastatin, colesevelam, ezetimibe, fenofibrate, fluvastatin, lovastatin, niacin, rosuvastatin, simvastatin and combinations thereof; and
  (c) at least one antihypertensive selected from chlorothiazide, chlorthalidone, hydrochlorothiazide, indapamide, metolazone, polythiazide, bumetanide, furosemide, torsemide, benazepril, captopril, enalapril, fosinopril, lisinopril, moexipril, perindopril, quinapril, ramipril, trandolapril, candesartan, eprosartan, irbesartan, losartan, olmesartan, tasosartan, telmisartan, valsartan, acebutolol, atenolol, betaxolol, bisoprolol, carvedilol, labetalol, metoprolol, nadolol, penbutolol, pindolol, propranolol, timolol, amlodipine, diltiazem, felodipine, isradipine, nicardipine, nifedipine, nisoldipine, verapamil and combinations thereof.

EXAMPLES

The following examples are merely illustrative, and do not limit this disclosure in any way. Reference is made in the examples to statistical analysis. Such reference is made in the interest of full disclosure and does not constitute admission that statistical significance is a prerequisite for patentability of any claim herein.

Example 1

Summary

The following is a protocol for a Phase II double blind placebo-controlled randomized study to investigate the safety and the hemodynamic effects of three-week oral applications of different doses of darusentan on top of standard medication in congestive heart failure patients.

Objectives

The primary objective of this study was to assess the tolerability and safety profile of three-week oral applications of different doses of darusentan on top of established standard medicinal treatments in patients suffering from advanced chronic congestive heart failure NYHA functional class III. Secondary objective was the assessment of the short-term effects of three-week darusentan treatment on hemodynamic parameters by means of SWAN GANZ floating catheterization and thermodilution.

Methodology

This was a multinational, multicenter, prospective, double-blind, placebo-controlled, randomized clinical trial.

After a pre-investigational eligibility check, double-blind treatment was started for a period of three weeks, followed by a one-week double-blind follow-up period.

The safety and hemodynamic effects of three different dosages of darusentan were consecutively studied, starting with darusentan at 30 mg or placebo. The following dosages of 300 mg followed by 100 mg were selected after reviewing the results and experiences gleaned from evaluating the safety data of at least 15 patients who completed the entire three-week dosing period.

Patients

To obtain at least 24 evaluable patients per treatment group, it was expected to include a total number of 120 patients into the study. Actually, 157 patients were randomized (30 mg: n=36; 100 mg: n=39; 300 mg: n=49; placebo: n=33).

Male and female patients were selected based on the following profile: aged 18 years or older who needed to undergo SWAN GANZ floating catheterization for diagnostic reasons with clinical CHF signs of at least three months duration and for any underlying cause (except for primary organic valvular heart disease), present or recent history of NYHA functional class III and presenting with a left ventricular ejection fraction less than or equal to 35%, assessed by means of echocardiography or isotope ventriculography within seven days prior to investigational procedures. Continuation in the study was only possible, if at baseline pulmonary capillary wedge pressure (PCWP) was more than equal to 12 mmHg and cardiac index (CI) was less than or equal to 2.6 l/min/m$^2$.

Test Product, Dose, Mode of Administration and Duration of Treatment

Tablets containing 30 mg, 100 mg or 300 mg darusentan.

Medication was taken orally once a day for 3 weeks

Reference Therapy, Dose, Mode of Administration and Duration of Treatment

Matching placebo tablets taken orally once a day for 3 weeks.

Criteria for Evaluation:
1. Efficacy
Changes in hemodynamic parameters from baseline focusing on CI ($1/min/m^2$), and PCWP (mmHg). Furthermore, pharmacokinetic parameters and neurohormone plasma levels were assessed.
2. Safety
Adverse events, changes in systemic blood pressure, heart rate, ECG and clinical laboratory parameters were measured.
Statistical Methods
All treated patients were included in the safety analysis. Efficacy was analyzed primarily according to the intention-to-treat principle. Continuous data were described by statistical characteristics (m, mean, standard deviation, minimum, $1^{st}$ quartile, median, $3^{rd}$ quartile, maximum, number of missing values) for each time point, as well as for changes from baseline. For categorical data and adverse events, frequency and percentage were given. For the two primary efficacy parameters CI ($1/min/m^2$) and PCWP (mmHg), analysis-of-covariance models were calculated.
Results:
During the course of this study blood glucose levels (mg/dl or mmol/l) were determined at patient visits. Only fasting blood glucose levels are shown below. "N/A" is used where either blood glucose level was not examined or the laboratory test was performed when the patient was not fasting.

diabetes mellitus (diabetes) and/or chronic kidney disease (CKD), do not reach guideline-recommended blood pressure goals.

The following is the protocol for a phase 3 randomized, double-blind, placebo-controlled, multi-center, parallel group study to evaluate the efficacy and safety of fixed doses of darusentan in subjects with resistant systolic hypertension receiving combination therapy with three or more antihypertensive drugs, including a diuretic.

| LIST OF ABBREVIATIONS | |
|---|---|
| ABPM | Ambulatory blood pressure monitoring |
| ACEI | Angiotensin converting enzyme inhibitor |
| AE | Adverse event |
| ALT | Alanine aminotransferase |
| ANCOVA | Analysis of covariance |
| ARB | Angiotensin receptor blocker |
| AST | Aspartate aminotransferase |
| AUC | Area-under-the-curve |
| AV | Atrioventricular |
| BMI | Body mass index |
| BNP | b-type natriuretic peptide |
| BP | Blood pressure |
| BUN | Blood urea nitrogen |
| CCB | Calcium channel blocker |
| $C_{max}$ | Peak plasma concentration |

| Glucose Levels | | | | | | | |
|---|---|---|---|---|---|---|---|
| | Visit 1 | Visit 2 | Visit 3 | Visit 4 | Visit 5 | Visit 6 | Side Effects |
| Patient 185 | N/A | 156 | N/A | N/A | N/A | 139 | Increasing of Dyspnoea (3) |
| | | | | | | | Increase of Body Weight (3) |
| | | | | | | | Decrease of Diuresis (3) |
| Patient 152 | N/A | 11.4 | 8.6 | 6.4 | 11.1 | 5.2 | Hyperglycemia (5) |
| | | | | | | | Face Rush (3) |
| | | | | | | | Pneumonia (3) |
| | | | | | | | Headache each day (2) |
| | | | | | | | Better Exercise Tolerance (2) |
| Patient 190 | N/A | 116 | 121 | N/A | N/A | N/A | Sensations of Heat (3) |
| | | | | | | | Head cephalgia (3) |
| | | | | | | | Angina Pectoris (3) |
| | | | | | | | Subjective feelings of unrest (3) |
| | | | | | | | Sleep Disturbance (3) |
| | | | | | | | Angina Pectoris with Dyspnoea (3) |
| | | | | | | | Sensations of Abdominal Pressure (3) |
| Patient 215 | N/A | 97 | 92 | N/A | N/A | N/A | CHF worsening (4) |
| Patient 216 | N/A | 127 | 141 | N/A | N/A | 104 | Acute Left Heart Failure (5) |
| | | | | | | | Decreasing Plueral Effusion |
| Patient 288 | 80 | 65 | N/A | N/A | N/A | 88 | None Listed |

Side Effect Relationship to Drug
(1) - Definite
(2) - Probable
(3) - Possible
(4) - Unlikely
(5) - Unrelated
**Non-survivor patients whose mordity was deemed to have an unlikely or unrelated relationship to darusentan by the clinician have been omitted.

Example 2

Summary

Hypertension clinical studies conducted over the last decade have indicated that proper control of systolic blood pressure (SBP) is equally as important as diastolic blood pressure (DBP) control in relationship to cardiovascular and renal outcomes; and SBP is more difficult to control than DBP, especially in patients over 50 years of age. Despite treatment with multiple antihypertensive drugs at therapeutic doses, a substantial number of patients, especially those with -continued

| LIST OF ABBREVIATIONS | |
|---|---|
| CHF | Chronic heart failure |
| CFR | Code of Federal Regulations |
| CKD | Chronic kidney disease |
| CNO | Certificate of non-objection |
| CRF | Case report form |
| DBP | Diastolic blood pressure |
| dL | Deciliters |
| DMC | Data Monitoring Committee |
| ECG | Electrocardiogram |
| eGFR | Estimated glomerular filtration rate |

LIST OF ABBREVIATIONS

| | |
|---|---|
| ET-1 | Endothelin-1 |
| $ET_A$ | Endothelin A receptor |
| $ET_B$ | Endothelin B receptor |
| ERA | Endothelin receptor antagonist |
| FDA | Food and Drug Administration |
| FSH | Follicle stimulating hormone |
| g | Grams |
| GCP | Good clinical practice |
| GDC | Global Data Collection |
| GGT | Gamma glutamyl aminotransferase |
| $HbA_{1c}$ | Glycosylated hemoglobin |
| HDL | High density lipoprotein |
| HIPAA | Health Insurance Portability and Accountability Act |
| HR | Heart rate |
| IB | Investigator's Brochure |
| ICD | Implantable cardioverter defibrillator |
| ICF | Informed Consent Form |
| ICH | International Conference on Harmonization |
| IEC | Independent ethics committee |
| IgM | Immunoglobulin M |
| IND | Investigational New Drug application |
| INR | International normalized ratio |
| IRB | Institutional review board |
| kg | Kilograms |
| $K_i$ | Inhibition constant |
| LDH | Lactate dehydrogenase |
| LDL | Low density lipoprotein |
| LFT | Liver function test |
| LH | Luteinizing hormone |
| LLN | Lower limit of normal |
| LV | Left ventricular |
| LVIDD | Left ventricular internal diastolic diameter |
| $m^2$ | Meters squared |
| MDRD | Modification of Diet in Renal Disease |
| mg | Milligrams |
| min | Minutes |
| mL | Milliliters |
| mmHg | Millimeters of mercury |
| µg | Micrograms |
| nM | Nanomolar |
| NOTEL | No toxic effect level |
| NOAEL | No observed adverse effect level |
| NSAIDs | Non-steroidal anti-inflammatory drugs |
| P450 | Cytochrome P450 |
| PDC | Premature Discontinuation |
| PDE | Phosphodiesterase |
| PHI | Protected health information |
| PK | Pharmacokinetic |
| po | Per os (orally) |
| PT | Prothrombin time |
| PTT | Partial thromboplastin time |
| qd | Once daily |
| RBC | Red blood cell |
| RHTN | Resistant hypertension |
| SADR | Serious adverse drug reaction |
| SAE | Serious adverse event |
| $SaO_2$ | Arterial oxygen saturation |
| SBP | Systolic blood pressure |
| SCr | Serum creatinine |
| SSRIs | Selective serotonin reuptake inhibitors |
| SUSAR | Suspected unexpected serious adverse event |
| $t_{1/2}$ | Elimination half-life |
| TCA | Tricyclic antidepressants |
| TG | Triglycerides |
| TSH | Thyroid stimulating hormone |
| UACR | Urinary albumin-to-creatinine ratio |
| ULN | Upper limit of normal |
| WBC | White blood cell |

Methods

Patients

Approximately 352 subjects will be randomized to one of three doses of darusentan (50, 100 or 300 mg po qd) or placebo in a ratio of 7:7:7:11 at approximately 160 investigative sites in North and South America, Europe, New Zealand, and Australia.

Eligible subjects will include men and women, 35-80 years old, treated with full doses of three or more antihypertensive drugs, including a diuretic, with RHTN as defined by contemporary clinical guidelines for the treatment of hypertension [1,2]. Subjects with diabetes and/or CKD must have a SBP ≥130 mmHg at Screening to be eligible for study entry. All other subjects must have a SBP of ≥140 mmHg. SBP at Screening must be <180 mmHg for all subjects. A BMI of 20 to 43 kg/m² or an upper arm circumference <42 cm, and an eGFR ≥30 mL/min/1.73 m² at Screening are also required. Subject eligibility will be reassessed at the initiation of the 2-week single-blind Placebo Run-in Period and at the Randomization Visit (see Study Schematic), and only those subjects who continue to meet inclusion/exclusion criteria at these visits will be randomized into the study. In particular, SBP and DBP measured at the Placebo Run-in Visit and at the Randomization Visit must be within 20 mmHg and 10 mmHg, respectively, of the values recorded at Screening in order for the subject to be eligible for randomization. NOTE: Subjects who fail to meet entry criteria after entering the placebo run-in phase will not be allowed to re-screen for the study.

All potential subjects will be classified with regard to diabetes and CKD as part of the Screening process. Diabetic subjects must have a documented diagnosis of Type 2 diabetes prior to Screening, and all screened subjects will be evaluated for the presence of CKD according to the following definition: (i) reduced excretory function with an eGFR <60 mL/min/1.73 m² and/or (ii) the presence of albuminuria in a spot urine sample (>200 mg/g [22.60 mg/mmol] creatinine).

Antihypertensive therapy must include:

A diuretic, preferably a thiazide; and

Two or more drugs from at least two of the following classes of antihypertensive agents:

ACEIs, ARBs, and/or renin inhibitors

CCBs beta-blockers central alpha-2 agonists peripheral alpha-1 antagonists direct vasodilators other centrally-acting drugs The combination of antihypertensive drugs administered should be consistent with current treatment guidelines [1,2]. For example, common multi-drug therapy may include a thiazide diuretic, an ACEI or an ARB, and a CCB. Subjects may be on more than 3 antihypertensive drugs at entry as long as the minimum requirements described above are met.

The minimum allowable dose of hydrochlorothiazide (HCTZ) will be 25 mg. For other thiazide-type diuretics, an equivalent dose to 25 mg HCTZ is also required. A loop diuretic may be substituted for the thiazide diuretic in subjects with CKD or a documented contraindication/intolerance to treatment with a thiazide. A potassium-sparing diuretic alone (e.g., triamterene) will not qualify as adequate diuretic therapy. The dose of each antihypertensive medication that the subject is receiving will be documented at Screening, and monitored throughout study participation. In addition, the dose of each concomitant antihypertensive medication will be classified at study entry according to the following criteria:

Highest labeled dose according to the product's package insert/labeling information for the applicable country/region Highest usual dose per clinical guidelines [1]

Highest tolerated dose

Highest appropriate dose for the subject per the Principal Investigator's best clinical judgment It is expected that subjects will have been optimized on their antihypertensive drug regimens well in advance of Screening for this study. Subjects must be stable on all antihypertensive drugs for at least 4 weeks prior to the Screening Visit. Adjustments to the number or dosage of concomitant antihypertensive medications will not be permitted at any time during the study, with the exception of protocol-allowed changes to diuretic therapy implemented to specifically address fluid retention-related events (see Study Design section below).

Subjects who meet any one of the following criteria will be deemed ineligible for participation in the study:

1. Subjects with an average sitting SBP of 180 mmHg or DBP of 110 mmHg.
2. Subjects with left ventricular (LV) systolic dysfunction as evidenced by a LV ejection fraction <40% and/or a LV internal diastolic diameter (LVIDD) >3.2 cm/m$^2$ or >6.0 cm, measured by echocardiogram at Screening (Visit 1) or within 3 months prior to Screening.
3. Subjects with a $HbA_{1c}$ >10% at Screening (Visit 1).
4. Subjects who have:
   a. A hemoglobin concentration <11.5 g/dL at Screening (Visit 1) or
   b. A hematocrit <34% at Screening (Visit 1)
5. Subjects with hypo- or hyperthyroidism, as evidenced by a serum thyroid stimulating hormone (TSH) concentration >1.5×ULN or <1.5× the lower limit of normal (LLN) at Screening (Visit 1).
6. Subjects with a serum ALT or AST >2×ULN at Screening (Visit 1).
7. Subjects with other identifiable secondary causes of resistant hypertension (e.g., parathyroid disease, pheochromocytoma, aortic coarctation, Cushing's disease, hyperaldosteronism).
8. Subjects who have experienced a myocardial infarction, unstable angina pectoris, or a cerebrovascular accident within 6 months of the Screening Visit (Visit 1).
9. Subjects with sick sinus syndrome or second or third degree atrioventricular (AV) block, chronic atrial fibrillation or recurrent atrial tachyarrhythmia (including paroxysmal atrial tachycardia), a history of recurrent ventricular tachycardia, or symptomatic bradycardia.
10. Subjects with implanted pacemakers or an implanted cardioverter defibrillator (ICD).
11. Subjects with a historical or current diagnosis of symptomatic or asymptomatic CHF, treated or untreated.
12. Subjects with hemodynamically significant valvular heart disease.
13. Subjects with Type 1 diabetes mellitus.
14. Subjects on hemodialysis or peritoneal dialysis at the time of Screening (Visit 1) and subjects with a history of solid organ transplant (e.g., kidney, heart).
15. Subjects who have had a diagnosis or recurrence of malignancy within the past 3 years, with the exception of basal cell carcinoma of the skin or in situ carcinoma of the cervix.
16. Subjects with sleep apnea are excluded, unless a post-treatment sleep study has confirmed treatment efficacy and there are no recordings of blood oxygen saturation ($SpO_2$) <90% at any time during the testing period.
17. Subjects who perform alternating shift or night work.
18. Women of childbearing potential or women who are pregnant or nursing.
19. Subjects not on stable doses of all concomitant medications for a minimum of 4 weeks prior to Screening, and subjects treated with any of the following prohibited medications:
    a. Oral or injected corticosteroids within 3 months of Screening (Visit 1). Systemic treatment with oral or injected steroids is also prohibited during study participation. NOTE: The use of inhaled steroids is allowed.
    b. Aspirin in excess of 325 mg per day.
    c. Chronic stable or unstable use of non-steroidal anti-inflammatory drugs (NSAIDS) other than aspirin is prohibited. Chronic use is defined as consecutive or non-consecutive days of treatment per week. (Note: In addition, the intermittent use of NSAIDs is strongly discouraged throughout the duration of this study. If intermittent treatment is required, NSAIDs must not be used for more than a total of 2 days during the single-blind Placebo Run-in Period or the 2 weeks prior to the Week 14 Visit [Visit 10a]. For all subjects requiring analgesic or anti-pyretic agents, the use of acetaminophen is recommended during study participation).
    d. Selective serotonin reuptake inhibitors (SSRIs), if a subject is not compliant with the medication and/or has not been receiving a stable dose for at least 3 months prior to Screening. In addition, SSRIs or similar drugs for the treatment of anxiety or depression may not be initiated at any time during the study.
    e. Tricyclic antidepressants (TCAs), if a subject is not compliant with the medication and/or has not been receiving a stable dose for at least 3 months prior to Screening. In addition, TCAs or similar drugs for the treatment of anxiety or depression may not be initiated at any time during the study.
    f. Another ERA (e.g., bosentan, sitaxsentan, atrasentan, TBC3711) at or within 6 months of Screening (Visit 1). In addition, subjects may not initiate treatment with another ERA at any time during the study.
    g. The use of short-acting oral nitrates (e.g., sublingual nitroglycerin) is permitted; however, subjects should not take short-acting oral nitrates within 4 hours of Screening (Visit 1) or any subsequent study visit.
    h. The use of long-acting oral nitrates (e.g., Isordil) is permitted; however, the dose must be stable for at least 2 weeks prior to Screening (Visit 1) and Randomization (Visit 3a).
    i. The use of oral sympathomimetic decongestants or β-agonists is permitted; however, not within 1 week prior to Screening (Visit 1), initiation of the Placebo Run-in (Visit 2), or Randomization (Visit 3a). In addition, use of these medications will be prohibited within 1 day prior to any clinic visit during study participation. NOTE: The stable chronic use of inhaled β-agonists is permitted. These drugs may be used as prescribed without the visit-based prohibitions described above.
    j. The use of theophylline is permitted; however, the dose must be stable for at least 4 weeks prior to Screening (Visit 1) and throughout study participation.
    k. The use of phosphodiesterase (PDE) type V inhibitors is permitted; however, subjects must refrain from taking these medications within three (3) days of Screening (Visit 1) or any subsequent study visit.
    l. Use of thiazolidinedione (i.e., glitazone) class of anti-diabetic medications (e.g., rosiglitazone, pioglitazone; alone or in combination pills) at or within 4 weeks of Screening (Visit 1). Subjects should not initiate treatment with thiazolidinediones at any time during the study.

Note: Subjects receiving exclusionary medications at Screening must undergo a minimum of 4 weeks washout prior to being re-screened for the study.
20. Subjects who have demonstrated non-compliance with previous medical regimens.
21. Subjects with a contraindication to treatment with an ERA. Contraindications include, but are not limited to, a history of elevated liver function tests (e.g., aminotransferases >2×ULN) or an event defined as a serious adverse event (SAE) attributed to previous treatment with an ERA.
22. Subjects who participated in a prior clinical study of darusentan and were randomized to, and received, active treatment.
23. Subjects who have participated in a clinical study involving another investigational drug or device within 4 weeks of the Screening Visit (Visit 1).
24. Subjects who have failed screening for this study two times.
25. Subjects who have any concomitant condition that, in the opinion of the investigator, may adversely affect the safety and/or efficacy of the study drug or severely limit the subject's lifespan or ability to complete the study (e.g., alcohol or drug abuse, disabling or terminal illness, mental disorders, institutionalization by judicial order).

Objectives

The primary objective of this study is to determine if darusentan is effective in reducing SBP and DBP in subjects with RHTN, despite treatment with full doses of three or more antihypertensive drugs, including a diuretic.

Secondary objectives of this study are to examine the effect of darusentan on mean 24-hour ambulatory blood pressure, percent of subjects meeting SBP goal, and eGFR. The safety and tolerability of darusentan in the subject population will also be evaluated.

Several measures of interest will also be examined.

Study Design

This is a Phase 3 randomized, double-blind, placebo-controlled, multi-center, parallel group study in subjects with RHTN, despite treatment with full doses of three or more antihypertensive drugs, including a diuretic.

The study will consist of three periods: Screening, Placebo Run-in, and Treatment. Screening assessments and evaluations may be conducted over a period of not more than 2 weeks. Following Screening, all eligible subjects will undergo a single-blind, Placebo Run-in of 2 weeks duration to ensure that blood pressure remains stable and continues to meet eligibility criteria for randomization. Subjects who continue to meet eligibility criteria following the 2-week Placebo Run-in Period will be randomized to one of four treatment groups (50, 100, or 300 mg of darusentan or placebo po qd), stratified by co-morbidity status (i.e., presence of diabetes and/or CKD versus the absence of these conditions) and race (i.e., Black versus non-Black). Subjects randomized to placebo or 50 mg darusentan will receive their randomized dose of study drug throughout the 14-week Treatment Period. Subjects randomized to 100 or 300 mg darusentan will be initiated on 50 mg for 2 weeks and will subsequently undergo up-titration to the next higher dose of darusentan every 2 weeks until the randomized dose is achieved (see FIG. 1). If a subject experiences a severe study drug-related AE during the Treatment Period, the subject's study drug dose may be reduced, according to investigator discretion. The choice to reduce the study drug dose may be made only once during the Treatment Period, and the change must be implemented prior to or at the Week 6 Visit. Once a subject's study drug dose has been down-titrated, it may not be subsequently increased. Subjects requiring down-titration of study drug after study Week 6 must discontinue treatment with study drug; however, the subject should remain in study through the end of the Treatment Period (i.e., Week 14). Study drug assignments will remain double-blinded throughout the Treatment Period. All subjects will receive a fixed dose of study drug for a minimum of 8 weeks prior to the evaluation of study endpoints at the Week 14 Visit.

Adjustments to the number or dosage of concomitant antihypertensive medications will not be permitted at any time during the study. However, if a subject develops signs or symptoms of fluid retention during the Treatment Period, manifested as peripheral edema and/or clinically significant weight gain between study visits that in the opinion of the investigator requires immediate treatment, the subject's diuretic therapy may be adjusted according to investigator discretion. It is recommended that a loop diuretic be added, or the dose increased for subjects already receiving a loop diuretic, prior to adjusting concomitant thiazide diuretic therapy. All changes will be documented in detail in the subject's case report form (CRF). Adjustment of diuretics will not be allowed within 2 weeks of the primary endpoint assessment.

Subjects who complete participation in the study through the Week 14 Visit, on or off study drug, will have the option to participate in a long-term safety extension study, with the exception of subjects who discontinue study drug due to a study drug-related AE. Subjects who discontinue treatment with study drug prior to the end of the Treatment Period due to a study drug-related AE will not be eligible to participate in the long-term safety extension study. Subjects who do not participate in the long-term safety extension study will discontinue treatment with study drug at the Week 14 Visit, and will return to the clinic for two safety visits prior to concluding study participation. Maximum placebo exposure in this study will be 16 weeks.

Women of childbearing potential will be excluded from study participation. Women who are surgically sterile or documented post-menopausal for at least 2 years are not considered to be of childbearing potential. Post-menopausal female subjects who are not surgically sterile will be required to use a double-barrier method of birth control throughout study participation. Serum alanine aminotransferase (ALT), aspartate aminotransferase (AST), alkaline phosphatase, gamma glutamyl aminotransferase (GGT), and total bilirubin will be monitored in all subjects throughout the study. All men will be required to provide blood samples for hormone analyses, and men who are able will be required to undergo semen analyses prior to and during treatment with study drug in order to evaluate the potential effects of darusentan on male fertility. Men who have had a vasectomy or who are unable to provide semen samples will be excused from this requirement.

Schedule of Assessments

| | STUDY VISIT | | | | | | | | | | | | |
|---|---|---|---|---|---|---|---|---|---|---|---|---|---|
| | 1 | 2 | 3a | 3b | 4 | 5 | 6 | 7 | 8 | 9 | 10a | 10b | |
| | | | Random. | | | | Study Week | | | | | 14 | |
| | −4 | −2 | D 1 | D 2 | 2 | 4 | 6 | 8 | 10 | 12 | D 1 | D 2 | UV[1] |
| Assessments | | | | | | | | | | | | | |
| Informed consent | X | | | | | | | | | | | | |
| Review Inclusion/Exclusion criteria | X | X | X | | | | | | | | | | |
| Medical history/demographics | X | | | | | | | | | | | | |
| ConMed assessment | X | X | X | | X | X | X | X | X | X | | X | X |
| Adverse Event assessment | | X | X | | X | X | X | X | X | X | | X | X |
| Trough sitting/standing BP and HR | X | X | X | | X | X | X | X | X | X | X | | X |
| Full physical examination | X | | | | | | | | | | X | | |
| Abbreviated physical examination | | X | X | | X | X | X | X | X | X | | | X |
| Measure body weight | X | X | X | | X | X | X | X | X | X | X | | X |
| 12-lead ECG | X | | X | | | X | | X | | | X | | |
| Echocardiogram | X[2] | | | | | | | | | | | | |
| Ambulatory BP Monitoring | | | on | off | | | | | | | on | off | |
| Health Economics Questionnaire | X[3] | | | | | | | | | | | | |
| Obtain vital status[4] | | | | | | | | | | | | | |
| Laboratory Tests | | | | | | | | | | | | | |
| Chemistry | X[5] | | X | | X | | X | | X | | X | | X |
| Hematology | X | | X | | X | | X | | X | | X | | X |
| Urine sample | X | | X | X[6] | X[6] | X[6] | X[6] | | | | X | X[6] | |
| Fasting Blood Collection[7] | | X, S | | | | | | | | S | | | |
| Trough PK plasma sample | | | X | | | | | | X | X | X | | |
| Biomarker plasma sample | | | X | | | | | | | | X | | |
| Women only: | | | | | | | | | | | | | |
| Serum pregnancy test | X | | | | | | | | | | X | | |
| β-hCG urine pregnancy test | | | X | | | | | | | | | | |
| Men only: | | | | | | | | | | | | | |
| Hormone analysis | | | X | | | | | | | | X | | |
| Semen analysis | | S[8] ■ ■ ■ (X) | | | | | | | | | S[8] ■ ■ ■ (X) | | |
| Warfarin-treated subjects only: | | | | | | | | | | | | | |
| Coagulation[9] | | | X | | | | | | | | x | | |
| Study Drug | | | | | | | | | | | | | |
| Collect study drug/assess compliance | | | X | | X | X | X | X | X | X | X | | X[10] |
| Register study visit | X | X | X | X | X | X | X | X | X | X | X | X | X |
| Randomization | | | | X | | | | | | | | | |
| Dispense study drug | | X[11] | | X[12] | X | X | X | X | X | | | | X[10] |

[1] UV = Unscheduled Visit;
[2] An echocardiogram must be obtained during the Screening Period or within 3 months prior to Screening. However, historical echocardiograms must report predefined criteria necessary to determine subject eligibility.
[3] A Health Economics Questionnaire will be completed by all screened subjects.
[4] All randomized subjects must be contacted to assess vital status at or shortly after the time of the last subject visit and again for the purposes of Global Data Collection.
[5] The chemistry panel performed at Screening will include measurements of immunoglobulin M (IgM), thyroid stimulation hormone (TSH) and glycosylated hemoglobin ($HbA_{1c}$). TSH and $HbA_{1c}$ will be used to evaluate subject eligibility.
[6] Spot urine collection for subjects with clinically significant albuminuria (≥30 mg/g [3.39 mg/mmol] creatinine) at Screening.
[7] S = Schedule. Fasting Blood Collection-Baseline may occur at Placebo Run-in (Visit 2) or within 2 weeks after that visit, but not at the Randomization Visit (Visit 3). Fasting Blood Collection-End of Study (EOS) for all subjects may occur within the 2 weeks following the Week 12 Visit (Visit 9), but not during the Week 14 Visit (Visit 10).
[8] Schedule a semen sample collection within 2 weeks prior to or during Randomization (Visit 3a). Schedule a post-baseline semen sample collection within 2 weeks prior to or during the Week 14 Visit (Visit 10a).
[9] Coagulation labs will be completed for subjects receiving warfarin (Coumadin) or warfarin-like anticoagulants.
[10] If down-titration of study drug occurs at an unscheduled visit, collection of study drug, assessment of compliance, and dispensation of study drug should also be performed.
[11] Single-blind, placebo study drug will be dispensed to all eligible subjects at this visit.
[12] Randomized, double-blind treatment begins for all eligible subjects.

Primary Efficacy Endpoints

The co-primary endpoints are the change from baseline to Week 14 in trough sitting SBP and trough sitting DBP, as measured by sphygmomanometry.

Secondary Endpoints

The following secondary endpoints will be assessed during this study:
Change from baseline to final measurement in mean 24-hour SBP measured by ABPM
Change from baseline to final measurement in mean 24-hour DBP measured by ABPM
The percent of subjects who reach SBP goal after 14 weeks of treatment, defined as follows:
Subjects with diabetes and/or CKD must reach a SBP goal of <130 mmHg
All other subjects must reach a SBP goal of <140 mmHg
Change from baseline to Week 14 in eGFR Measures of Interest The following measures of interest will be examined:
Change from baseline in the following ABPM measures:
Mean hourly ambulatory SBP and DBP over a 24-hour monitoring period
Mean trough ambulatory SBP and DBP
Mean peak ambulatory SBP and DBP
Mean trough/peak ratio
Mean daytime ambulatory SBP and DBP
Mean nighttime ambulatory SBP and DBP
Mean daytime/nighttime ratio;
Change from baseline to Week 14 in pulse pressure measured by sphygmomanometry;
Change from baseline in selected biomarker concentrations;
Change from baseline in glycosylated hemoglobin ($HbA_{1c}$), fasting plasma glucose, serum lipid profile, serum insulin, serum C-peptide, serum C-reactive protein, and waist circumference;
Change from baseline in urinary albumin-to-creatinine ratio (UACR) in a subset of subjects with clinically significant albuminuria (i.e., ≥30 mg/g [3.39 mg/mmol] creatinine in a spot urine sample);
Trough plasma concentrations of darusentan and its metabolites;

Statistical Methods

Change in SBP and DBP from baseline to Week 14 will be tested with analysis of covariance, using stratification factors (comorbidity status and race) and baseline blood pressure as covariates. Proportion at goal blood pressure will be tested with logistic regression, using the same covariates. The last observation during double blind therapy will be used for analyses.

Adjustment for multiple comparisons for the primary endpoints of change in SBP and DBP will use the fallback method. First, SBP will be compared between the 300 mg dose and placebo at the nominal alpha level of 0.04. If this is significant, DBP will be compared between the 300 mg dose and placebo at the nominal level of 0.04. From this point, the fixed sequence procedure will be followed, requiring significance on an endpoint before allowing testing of the following endpoint, and testing all comparisons at the same level. If the 300 mg dose was significant at the 0.04 level for both SBP and DBP, the tests will be reported at the 0.05 level; otherwise the tests will be reported at the 0.01 level. These comparisons will be, in order, the 100 mg dose compared to placebo for SBP then DBP, and the 50 mg dose compared to placebo for SBP and then DBP. Continuous secondary endpoints will be handled analogously.

Assuming a difference in placebo-adjusted change from baseline of 8 mmHg in trough SBP for each darusentan dose and a standard deviation of 15 mmHg, 121 subjects randomized to placebo and 77 subjects randomized to each dose of darusentan will provide 85-90% power to detect a difference between placebo and any individual darusentan dose, and 95% power to find at least one dose of darusentan that is different from placebo.

It is expected that treatment of a human subject, for example a human subject having diabetic nephropathy and/or metabolic syndrome, in accordance with the foregoing protocol will produce an enhancement in glycemic control and/or insulin sensitivity.

REFERENCES

[1] Chobanian A V, Bakris G L, Black H R, Cushman W C, Green L A, Izzo J L, Jr. et al. Seventh report of the Joint National Committee on Prevention, Detection, Evaluation, and Treatment of High Blood Pressure. Hypertension 2003; 42(6):1206-1252.
[2] 2003 European Society of Hypertension-European Society of Cardiology Guidelines for the Management of Arterial Hypertension. J Hypertens 2003; 21(6):1011-1053.

All patents and publications cited herein are incorporated by reference into this application in their entirety.

The words "comprise", "comprises", and "comprising" are to be interpreted inclusively rather than exclusively.

What is claimed is:

1. A method for treating diabetic nephropathy in a human subject in need of such treatment, said method comprising:
administering to the subject atrasentan or a salt thereof, and a dose of at least one angiotensin converting enzyme inhibitor or an angiotensin II receptor blocker.

2. The method of claim 1, comprising administering the dose of the angiotensin converting enzyme inhibitor or angiotensin II receptor blocker at an adequate dose labeled for a hypertension indication.

3. The method of claim 1, comprising administering the dose of the angiotensin converting enzyme inhibitor or angiotensin II receptor blocker at a highest dose labeled for a hypertension indication.

4. The method of claim 1, comprising administering the dose of the angiotensin converting enzyme inhibitor or angiotensin II receptor blocker at a highest usual dose prescribed according to Joint National Committee on Prevention, Detection, Evaluation, and Treatment of High Blood Pressure (JNC7), British Hypertensive Society (BHD-IV), European Society of Hypertension/European Society of Cardiology (ESH/ESC) or World Health Organization/International Society of Hypertension (WHO/ISH) guidelines.

5. The method of claim 1, comprising administering the dose of the angiotensin converting enzyme inhibitor or angiotensin II receptor blocker at a highest tolerated dose in the human subject.

6. The method of claim 1, wherein the angiotensin converting enzyme inhibitor is selected from the group consisting of alacepril, benzapril, captopril, ceronapril, cilazapril, delapril, enalapril, enalaprilat, eosinopril, fosinopril, imidapril, lisinopril, moexipril, moveltipril, omapatrilat, perindopril, quinapril, ramipril, sampatrilat, spirapril, temocapril, trandolapril, and combinations thereof.

7. The method of claim 1, wherein the angiotensin II receptor blocker is selected from the group consisting of candesartan, eprosartan, irbesartan, losartan, olmesartan, tasosartan, telmisartan, valsartan and combinations thereof.

8. The method of claim 1, wherein the method further comprises administering a thiazide diuretic selected from the group consisting of althiazide, bendroflumethiazide, benzthiazide, benzyl hydrochlorothiazide, buthiazide, chlorothiazide, chlorthalidone, cyclopenth iazide, ethiazide, fenquizone, hydrochlorothiazide, hydroflumethiazide, indapamide, methyclothiazide, metolazone, paraflutizide, polythiazide, quinethazone, teclothiazide, trichlormethiazide, and combinations thereof.

9. The method of claim 1, wherein the method further comprises administering a loop diuretic selected from the group consisting of bumetanide, furosemide, torsemide and combinations thereof.

10. The method of claim 1, wherein the diabetic nephropathy is overt diabetic nephropathy.

11. The method of claim 1, wherein the diabetic nephropathy is caused by Type II diabetes.

12. The method of claim 1, wherein the human subject is diagnosed with Type II diabetes.

13. The method of claim 1, comprising administering atrasentan or salt thereof for a period of at least 3 months.

14. The method of claim 1, comprising administering the atrasentan or a salt thereof for as long as a therapeutic benefit is provided thereby and any adverse side effect thereof remains commensurate with the therapeutic benefit.

15. The method of claim 1, wherein the atrasentan or salt thereof is administered concomitantly with the angiotensin converting enzyme inhibitor or angiotensin II receptor blocker.

16. A method of treating diabetic nephropathy in a human subject in need of treatment comprising:
administering to the subject atrasentan or a salt thereof, and a dose of at least one of an angiotensin converting enzyme inhibitor or an angiotensin II receptor blocker, and
wherein the method results in a beneficial effect on one or more morphological markers of diabetic nephropathy.

17. The method of claim 16, wherein the morphologic marker of diabetic nephropathy is glomerulosclerosis.

18. A method of treating diabetic nephropathy in a human subject in need of treatment comprising:
administering to the subject atrasentan or a salt thereof, and a dose of at least one of an angiotensin converting enzyme inhibitor or an angiotensin II receptor blocker, and
wherein the method results in a beneficial effect on one or more indicators of renal function.

19. The method of claim 18, wherein the indicator of renal function is albuminuria.

20. The method of claim 19, wherein the beneficial effect on albuminuria is a reduction in albuminuria.

21. The method of claim 18, wherein the indicator of renal function is urinary albumin-to-creatinine ratio (UACR).

22. The method of claim 21, wherein the beneficial effect on urinary albumin-to-creatinine ratio (UACR) is a reduction in urinary albumin-to-creatinine ratio (UACR).

23. The method of claim 18, wherein the indicator of renal function is glomerular filtration rate.

24. The method of claim 23, wherein the beneficial effect on glomerular filtration rate is an increase in glomerular filtration rate.

25. The method of claim 18, wherein the indicator of renal function is creatinine clearance.

26. The method of claim 25, wherein the beneficial effect on creatinine clearance is an increase in creatinine clearance.

27. The method of claim 25, wherein the beneficial effect on creatinine clearance is a reduction in serum creatinine.

28. The method of claim 19, wherein the beneficial effect on albuminuria is a reduction in the rate of increase of albuminuria compared to a baseline albuminuria.

29. The method of claim 21, wherein the beneficial effect on urinary albumin-to-creatinine ratio (UACR) is a reduction in the rate of increase of urinary albumin-to-creatinine ratio (UACR) compared to a baseline urinary albumin-to-creatinine ratio (UACR).

30. The method of claim 23, wherein the beneficial effect on glomerular filtration rate is a reduction in the rate of decrease of glomerular filtration rate compared to a baseline glomerular filtration rate.

31. The method of claim 25, wherein the beneficial effect on creatinine clearance is a reduction in the rate of decrease of creatinine clearance compared to a baseline creatinine clearance.

32. The method of claim 25, wherein the beneficial effect on creatinine clearance is a reduction in the rate of increase of serum creatinine.

* * * * *